United States Patent
Jin et al.

(10) Patent No.: US 11,369,347 B2
(45) Date of Patent: Jun. 28, 2022

(54) PORTABLE ULTRASONIC DIAGNOSTIC APPARATUS AND METHOD OF CONTROLLING THE SAME

(71) Applicant: SAMSUNG MEDISON CO., LTD., Hongcheon-gun (KR)

(72) Inventors: Gil-Ju Jin, Seoul (KR); Mi Jeoung Ahn, Seoul (KR); Yuri Kim, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 1007 days.

(21) Appl. No.: 14/854,106

(22) Filed: Sep. 15, 2015

(65) Prior Publication Data
US 2016/0157822 A1     Jun. 9, 2016

Related U.S. Application Data

(60) Provisional application No. 62/088,014, filed on Dec. 5, 2014.

(30) Foreign Application Priority Data

May 29, 2015     (KR) ........................ 10-2015-0075917

(51) Int. Cl.
  *A61B 8/00*     (2006.01)
  *G06F 1/16*     (2006.01)
  (Continued)

(52) U.S. Cl.
  CPC ................ *A61B 8/462* (2013.01); *A61B 8/14* (2013.01); *A61B 8/4427* (2013.01);
  (Continued)

(58) Field of Classification Search
CPC .. A61B 8/00; A61B 8/462; A61B 8/54; A61B 8/467; A61B 8/465; A61B 8/14;
(Continued)

(56) References Cited

U.S. PATENT DOCUMENTS 6,117,085 A * 9/2000 Picatti ................. G01S 7/52017
                                                                600/459
9,072,471 B2    7/2015 Kato et al.
(Continued)

FOREIGN PATENT DOCUMENTS

EP     2 698 686 A2    2/2014
EP     2698686 A2      2/2014
(Continued)

OTHER PUBLICATIONS

Communication dated May 9, 2016, issued by the European Patent Office in counterpart European Application No. 15181413.4.
(Continued)

*Primary Examiner* — Sean D Mattson
(74) *Attorney, Agent, or Firm* — Morgan, Lewis & Bockius LLP

(57) ABSTRACT

A portable ultrasonic diagnostic apparatus and a method of controlling the same are provided, including a flexible display and a controller which changes a layout of an image displayed on the flexible display. An image necessary for diagnosing an object is appropriately disposed on a flexible display according to a situation, and thus, the user can intuitively determine an ultrasonic image.

25 Claims, 28 Drawing Sheets

(51) Int. Cl.
*G06F 3/147* (2006.01)
*A61B 8/14* (2006.01)
*G01S 7/52* (2006.01)

(52) U.S. Cl.
CPC ............ *A61B 8/4472* (2013.01); *A61B 8/465* (2013.01); *A61B 8/467* (2013.01); *A61B 8/54* (2013.01); *G01S 7/52085* (2013.01); *G06F 1/1652* (2013.01); *G06F 3/147* (2013.01); *G09G 2340/14* (2013.01); *G09G 2380/02* (2013.01); *G09G 2380/08* (2013.01)

(58) Field of Classification Search
CPC ....... A61B 8/4472; A61B 8/4427; G01S 7/00; G01S 7/52085; G06F 1/00; G06F 3/00; G06F 3/147; G06F 1/1652; G09G 2340/00; G09G 2380/00; G09G 2340/14; G09G 2380/08; G09G 2380/02
See application file for complete search history.

(56) References Cited

U.S. PATENT DOCUMENTS

| | | | |
|---|---|---|---|
| 9,646,407 | B2 | 5/2017 | Lee et al. |
| 9,886,100 | B2 | 2/2018 | Jung et al. |
| 10,617,391 | B2 | 4/2020 | Yang et al. |
| 2003/0125629 | A1 | 7/2003 | Ustuner |
| 2004/0267122 | A1* | 12/2004 | Nadadur ................. A61B 8/465 600/440 |
| 2006/0034042 | A1* | 2/2006 | Hisano .................. G06F 1/1616 361/679.04 |
| 2006/0238494 | A1 | 10/2006 | Narayamaswami et al. |
| 2007/0073148 | A1* | 3/2007 | Kim ....................... A61B 8/466 600/437 |
| 2007/0125189 | A1 | 6/2007 | Bossi et al. |
| 2010/0049050 | A1* | 2/2010 | Pelissier ................. A61B 8/00 600/443 |
| 2010/0053173 | A1* | 3/2010 | Cohen .................... G09G 3/344 345/501 |
| 2010/0120470 | A1* | 5/2010 | Kim ....................... G06F 1/1626 455/566 |
| 2012/0038613 | A1* | 2/2012 | Choi ...................... G06F 1/1652 345/211 |
| 2012/0172726 | A1* | 7/2012 | Sakai ..................... A61B 8/465 600/443 |
| 2012/0310094 | A1* | 12/2012 | Miyachi ................. A61B 8/469 600/443 |
| 2013/0012817 | A1* | 1/2013 | Ahn ...................... A61B 8/4427 600/441 |
| 2013/0127918 | A1* | 5/2013 | Kang .................... G06F 3/0481 345/660 |
| 2013/0176248 | A1* | 7/2013 | Shin ........................ G06F 3/041 345/173 |
| 2013/0184582 | A1* | 7/2013 | Kanayama ............. A61B 8/463 600/440 |
| 2013/0215041 | A1* | 8/2013 | Kim ...................... G06F 3/0487 345/173 |
| 2014/0005550 | A1* | 1/2014 | Lu .......................... A61B 8/465 600/459 |
| 2014/0098095 | A1* | 4/2014 | Lee ........................ G06F 3/041 345/420 |
| 2014/0247252 | A1* | 9/2014 | Lee .......................... G09G 3/20 345/204 |
| 2014/0282142 | A1* | 9/2014 | Lin ........................ A61B 8/461 715/765 |

FOREIGN PATENT DOCUMENTS

| | | |
|---|---|---|
| EP | 2 786 708 A1 | 10/2014 |
| EP | 2786708 A1 | 10/2014 |
| ER | 2 796 976 B1 | 1/2020 |
| JP | 2010-099122 A | 5/2010 |
| JP | 2013-111203 A | 6/2013 |
| KR | 10-2013-0080937 A | 7/2013 |
| KR | 10-2014-0032767 A | 3/2014 |
| KR | 10-2014-0039954 A | 4/2014 |
| KR | 10-2014-0044665 A | 4/2014 |
| KR | 10-2014-0112988 A | 9/2014 |

OTHER PUBLICATIONS

Communication dated Mar. 19, 2018, issued by the European Patent in counterpart European Application No. 15 181 413.4.
Communication dated Nov. 12, 2018, issued by the European Patent Office in counterpart European Application No. 18193963.8.
Young-Rock HA, "Initial evaluation of a trauma patient using an ultrasound," J Korean Med Assoc, English Nov. 2012, 55(11), pp. 1097-1112.
Korean Office Action dated Dec. 15, 2021 issued in Korean Patent Application No. 10-2015-0075917 (with English translation).

* cited by examiner

FIG.6
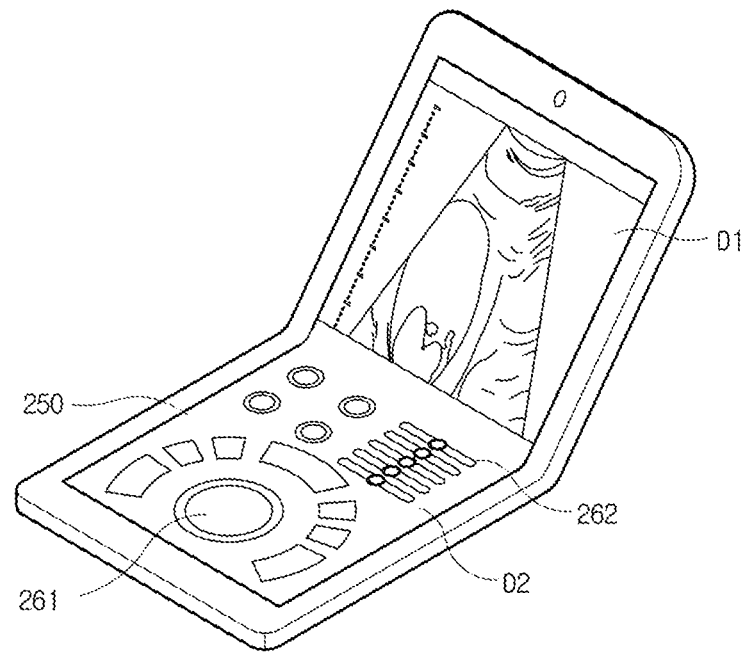
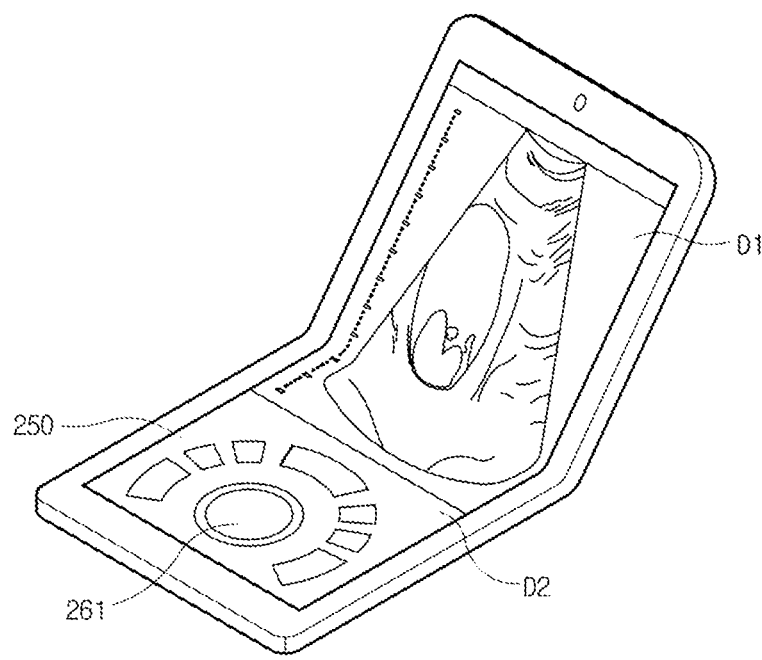

FIG. 7
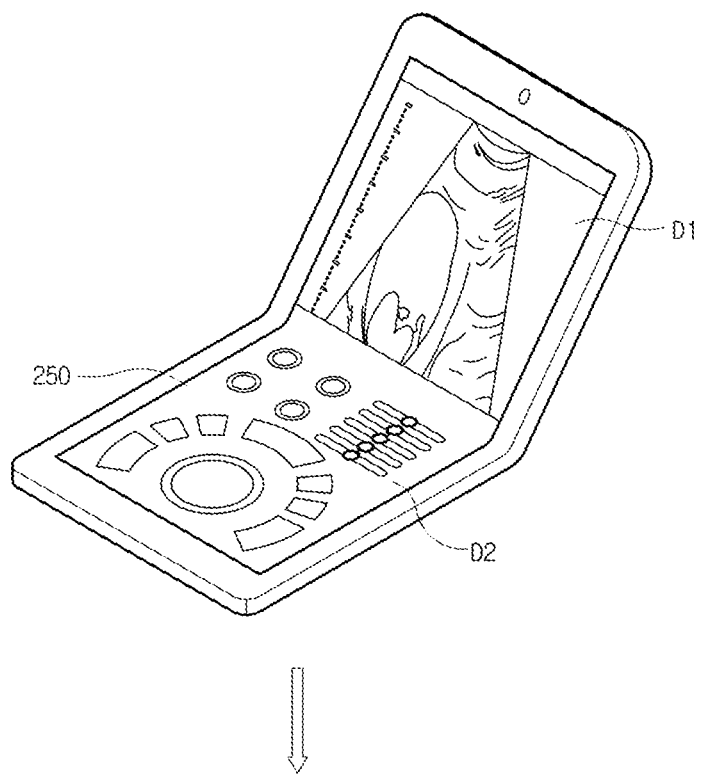
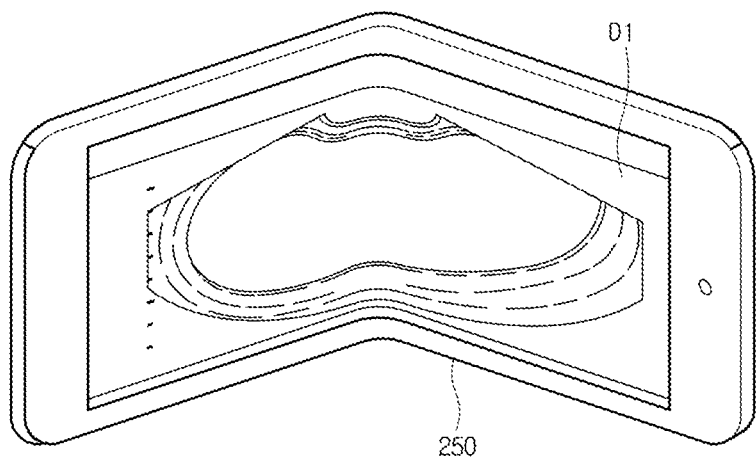

FIG. 8
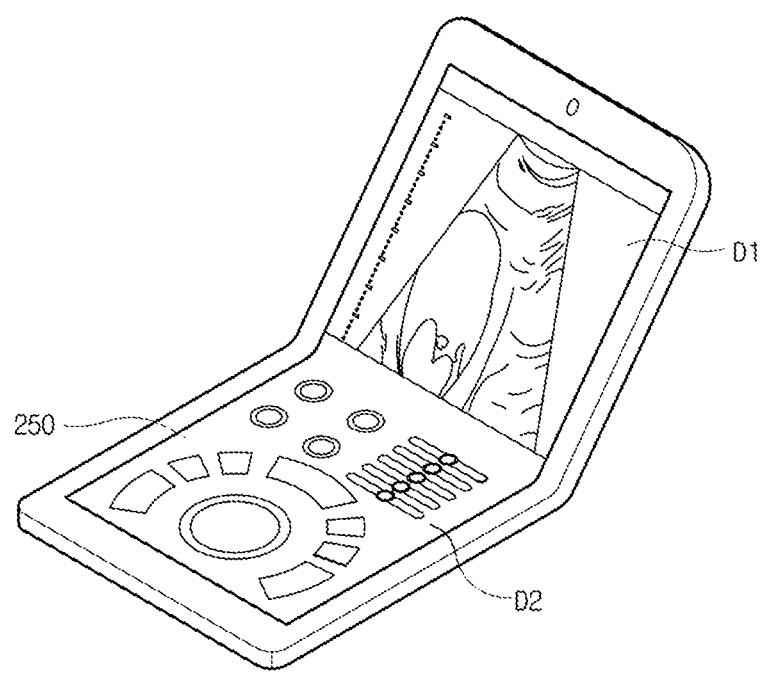
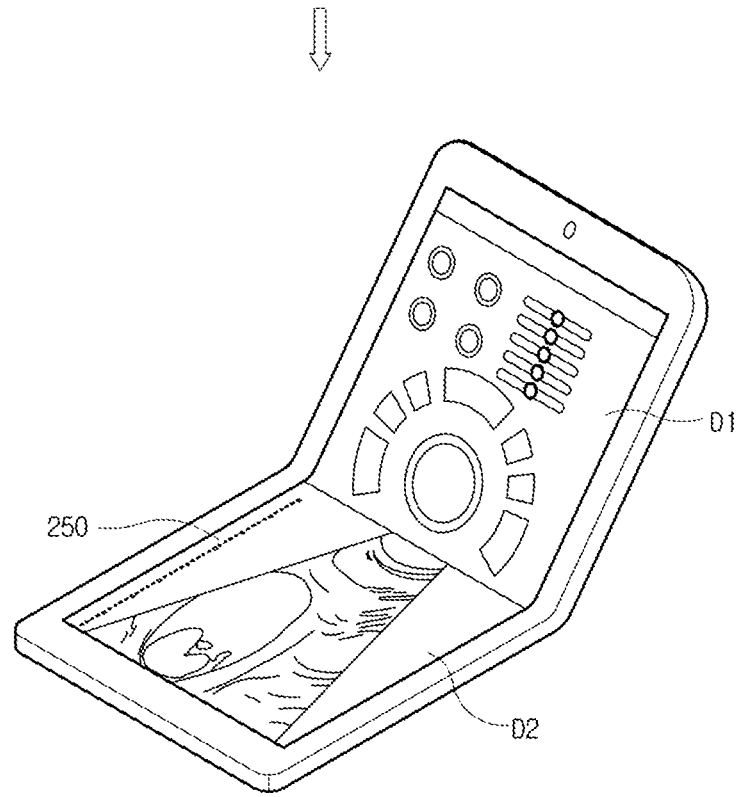

FIG. 11
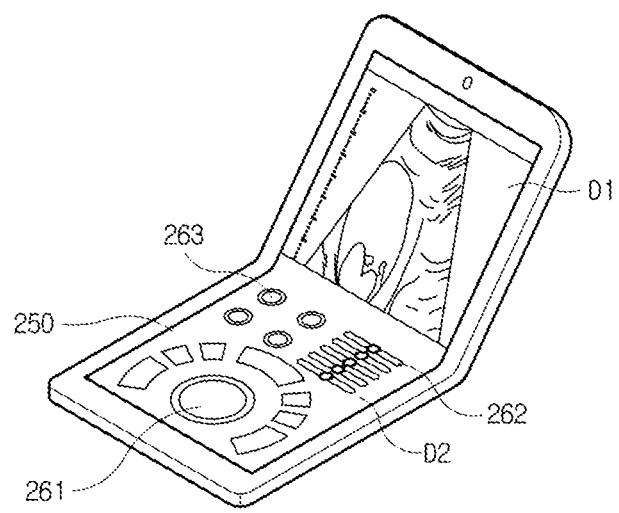
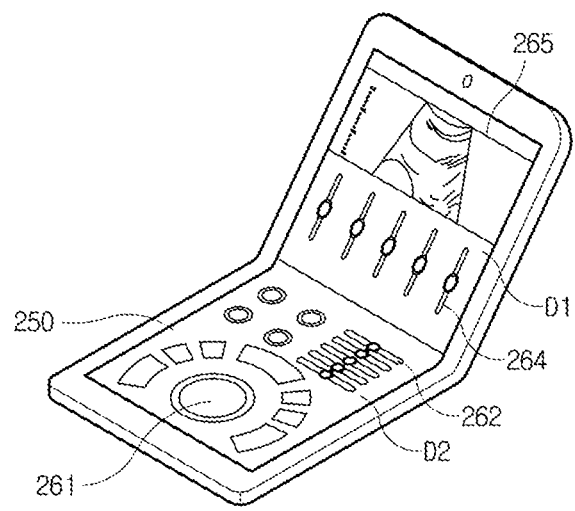

FIG. 12
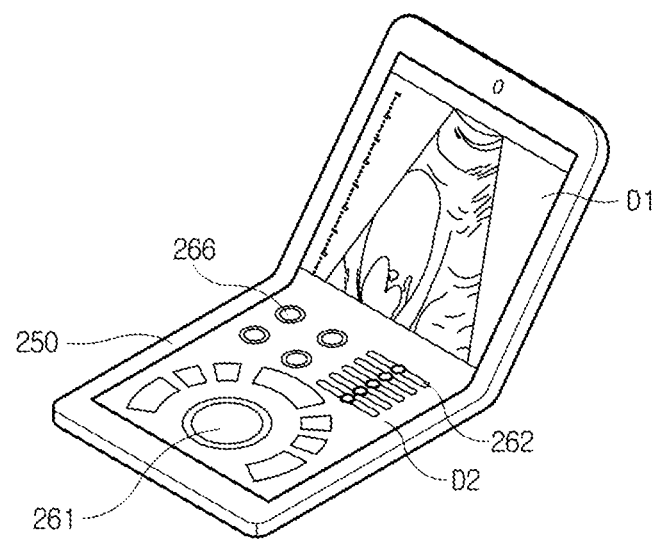
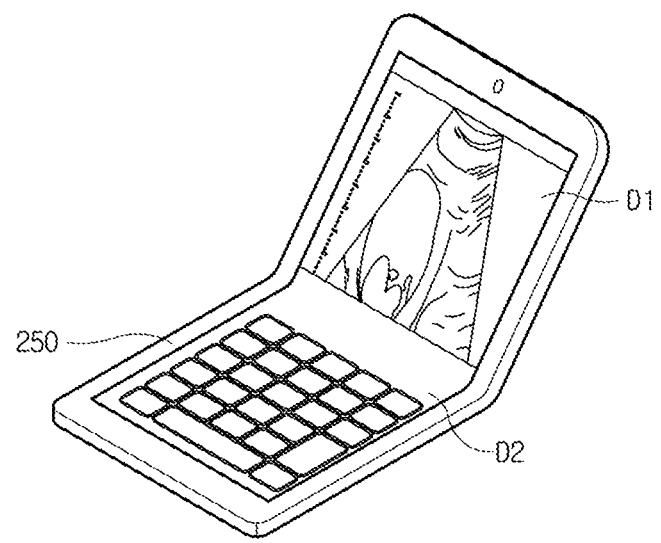

FIG. 23
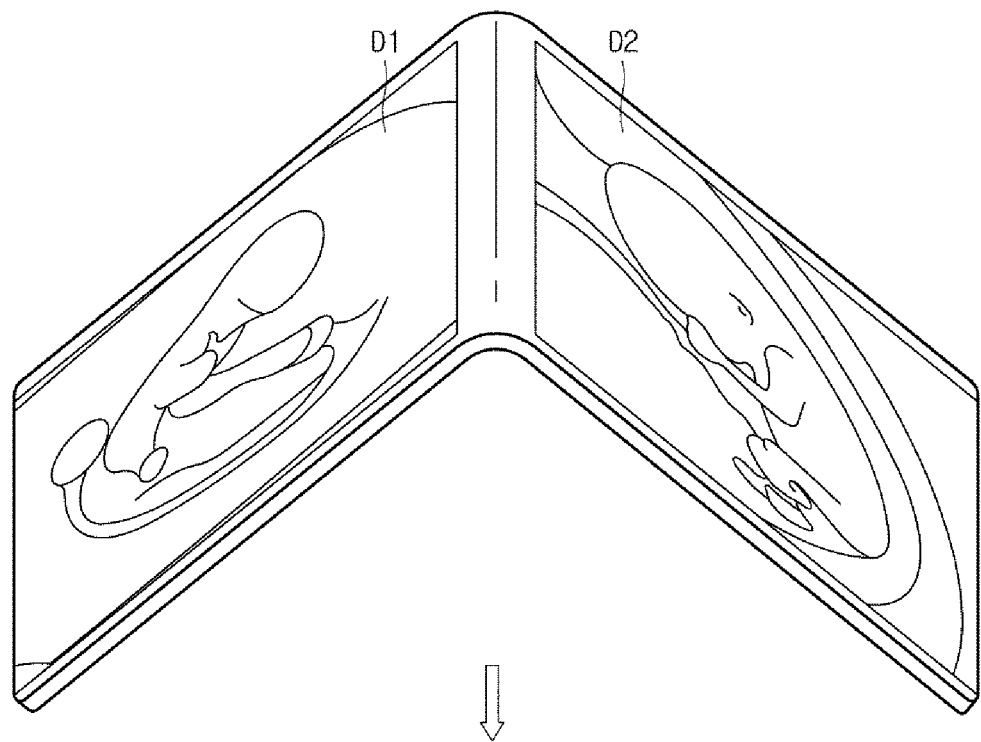
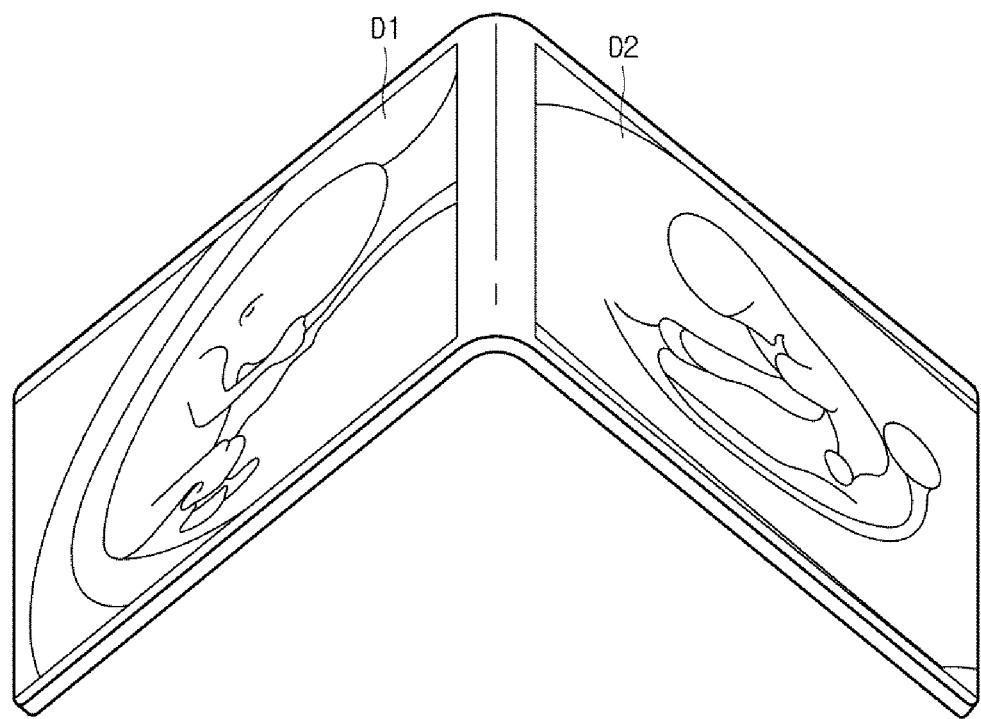

PORTABLE ULTRASONIC DIAGNOSTIC APPARATUS AND METHOD OF CONTROLLING THE SAME

CROSS-REFERENCE TO RELATED APPLICATION

This application claims priority from Korean Patent Application No. 10-2015-0075917, filed on May 29, 2015 in the Korean Intellectual Property Office and U.S. Patent Application 62/088,014, filed on Dec. 5, 2014 in the United States Patent and Trademark Office, the disclosure of which is incorporated herein in its entirety by reference.

BACKGROUND

1. Field

Apparatuses and methods consistent with exemplary embodiments relate to a portable ultrasonic diagnostic apparatus and a method of controlling the same.

2. Description of the Related Art

The ultrasonic imaging apparatuses are apparatuses that each apply an ultrasonic wave toward a target area inside an object from a surface of the object, receive a reflected echo ultrasonic wave, and obtain a tomogram of a soft tissue or an image of a blood flow in a non-invasive manner.

The ultrasonic imaging apparatuses are advantageous in that they are small and cheap, and can display diagnostic images in real time compared to other image diagnostic apparatuses such as X-ray diagnostic apparatuses, computerized tomography (CT) scanners, magnetic resonance imaging (MRI) apparatuses, etc. Due to these advantages, the ultrasonic imaging apparatuses are being widely used.

Among the ultrasonic imaging apparatuses, there are portable ultrasonic diagnostic apparatuses that each include a probe which transmits and receives an ultrasonic wave and a main body including a display unit which displays various contents based on a signal received from the probe and a controller which controls operations of the display unit and other components, and have portability and mobility.

SUMMARY

One or more exemplary embodiments provide a portable ultrasonic diagnostic apparatus, which changes a layout of an image displayed on a flexible display, and a method of controlling the same.

Additional aspects of the invention will be set forth in part in the description which follows and, in part, will be obvious from the description, or may be learned by practice of the invention.

In accordance with one aspect of the present invention, a portable ultrasonic diagnostic apparatus includes a flexible display and a controller which changes a layout of an image displayed on the flexible display.

The flexible display may display at least one of an ultrasonic image and a control panel which receives a control command of the portable ultrasonic diagnostic apparatus on one or more display areas.

The controller may extend, shrink, move, rotate, power-on, or power-off one or more display areas of the flexible display.

The controller may enlarge, reduce, rotate, or change the image displayed on the flexible display.

The portable ultrasonic diagnostic apparatus may further include a probe which transmits or receives an ultrasonic wave and generates an electrical signal corresponding to the received ultrasonic wave, and the controller, when the controller receives the electrical signal, may change the layout of the image.

The portable ultrasonic diagnostic apparatus may further include an input unit which receives a layout change command from a user, and the controller may change the layout of the image according to the layout change command.

The input unit may include an emergency mode button, and the flexible display, when the emergency mode button is selected, may display an emergency mode image which provides a guide for emergency situation to the user.

The emergency mode image may include an image which indicates a position of a diagnosis portion of an object.

The flexible display, when the emergency mode button is selected, may display an image which indicates a position of a diagnosis portion of an object based on at least one of a focused assessment with sonography for trauma (FAST) pericardial, perihepatic, perisplenic, and pelvic (4Ps) reference and a FAST airway, breathing, circulation, and disability (ABCD) reference.

The input unit may include an emergency mode button, and the flexible display, when the emergency mode button is selected, may display a text which provides a guide for emergency situation to the user.

The portable ultrasonic diagnostic apparatus may further include a sensor which detects a physical change of the flexible display, and the controller may change the layout of the image according to a detecting signal of the sensor.

The sensor may include a contact sensor which detects contact of both ends of the flexible display.

The controller may power off the flexible display when the contact sensor detects the contact of the both ends, and display each of an ultrasonic image and a control panel which receives a control command of the portable ultrasonic diagnostic apparatus on each of a plurality of areas of the flexible display when the contact sensor does not detect the contact of the both ends.

The sensor may include an angle sensor which detects a bending degree of the flexible display.

The controller may extend or shrink a display area in which an image of the flexible display is displayed based on a detection signal of the angle sensor.

The controller, when the flexible display is bent a preset angle or more, may control so as to display the same plane of the same object on a first area and second area of the flexible display.

The controller, when the flexible display is bent a preset angle or more, may control so as to display each of front and rear surfaces or left and right surfaces of a three-dimensional image, or a current image and a past image on a first area and second area of the flexible display.

The sensor may include at least one of a gyro sensor, an acceleration sensor, a pressure sensor, and a temperature sensor.

The flexible display may be implemented using a touch screen and may display a control panel which receives a control command from the user through a user interface.

The control panel may implement at least one of a keyboard, a mouse, a trackball, a time gain compensation (TGC) control knob, a lateral gain compensation (LGC) control knob, and a paddle as the user interface.

The controller may change the user interface implemented by the control panel.

The portable ultrasonic diagnostic apparatus may further include a freeze button which stops an ultrasonic image displayed on the flexible display.

The portable ultrasonic diagnostic apparatus may further include a wireless probe which transmits or receives an ultrasonic wave and generates an electrical signal corresponding to the received ultrasonic wave.

The wireless probe may include a beamformer which applies a time delay to the ultrasonic wave.

The portable ultrasonic diagnostic apparatus may further include an input unit which receives a control command which simultaneously controls a plurality of display areas of the flexible display from a user.

The flexible display and the controller may be implemented in a portable computer or a portable terminal.

In accordance with another aspect of the present invention, a method of controlling a portable ultrasonic diagnostic apparatus includes changing a layout of an image displayed on a flexible display, and displaying at least one of an ultrasonic image and a control panel which receives a control command of the portable ultrasonic diagnostic apparatus on the flexible display according to the changed layout.

BRIEF DESCRIPTION OF THE DRAWINGS

These and/or other aspects of the invention will become apparent and more readily appreciated from the following description of the embodiments, taken in conjunction with the accompanying drawings of which:

FIGS. 6 to 12 are diagrams illustrating various examples of a flexible display of which a layout is changed according to a control signal of a system controller;

FIGS. 21 to 23 are diagrams for describing examples of a flexible display of which a layout is changed according to a control signal;

DETAILED DESCRIPTION

Figure 1A:
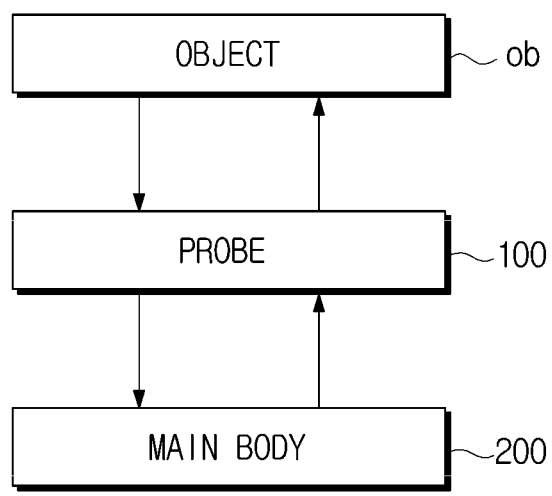
FIGS. 1A and 1B are control block diagrams illustrating a portable ultrasonic diagnostic apparatus in accordance with one exemplary embodiment.

Reference will now be made in detail to the exemplary embodiments, examples of which are illustrated in the accompanying drawings, wherein like reference numerals refer to like elements throughout.

Hereinafter, a configuration of a portable ultrasonic diagnostic apparatus in accordance with one exemplary embodiment will be described with reference to FIGS. 1A to 3.

Figure 1B:
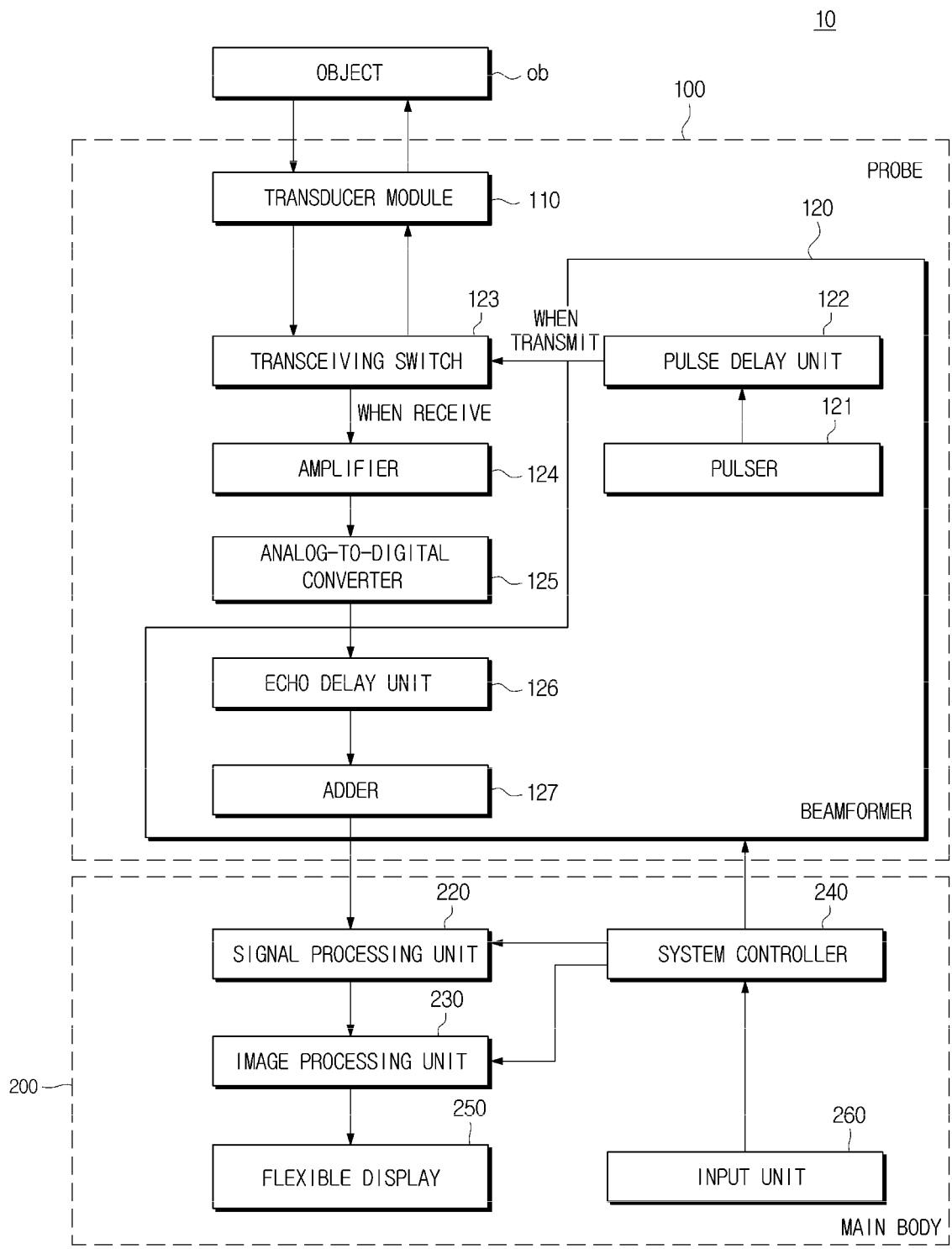
Figure 2:
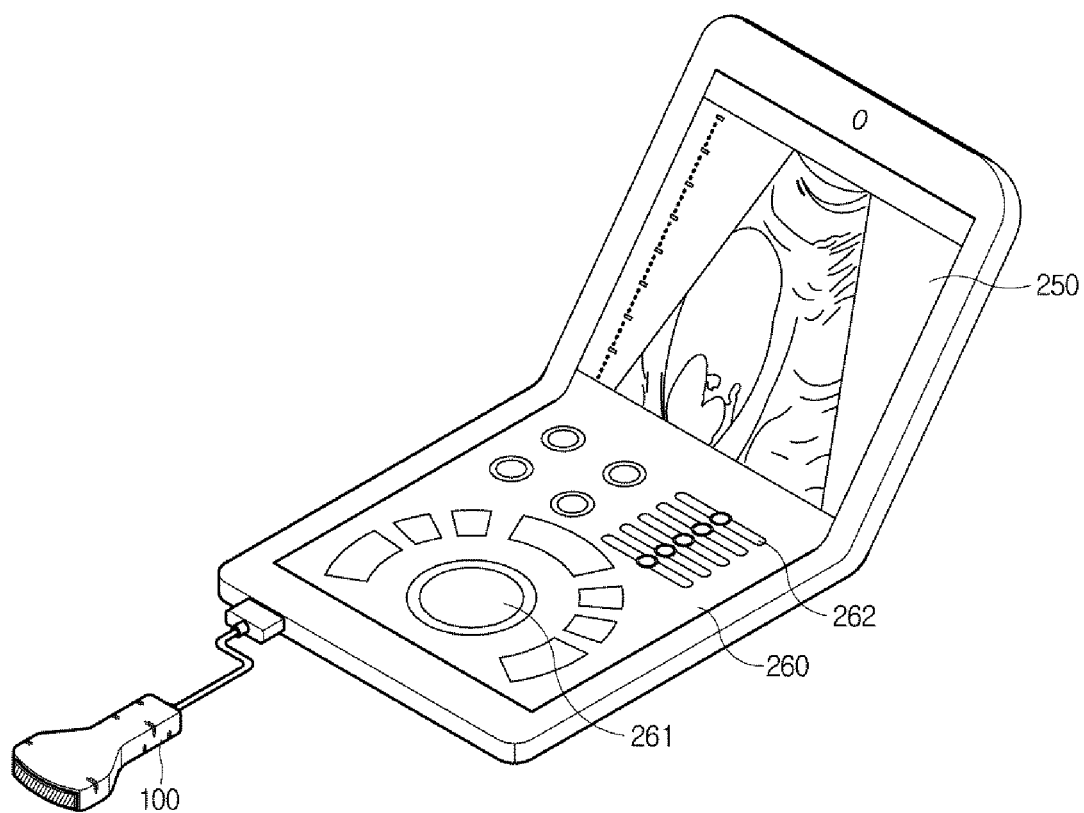
FIGS. 2 and 3 are diagrams illustrating exteriors of portable ultrasonic diagnostic apparatuses in accordance with respective other exemplary embodiments.
Figure 3:
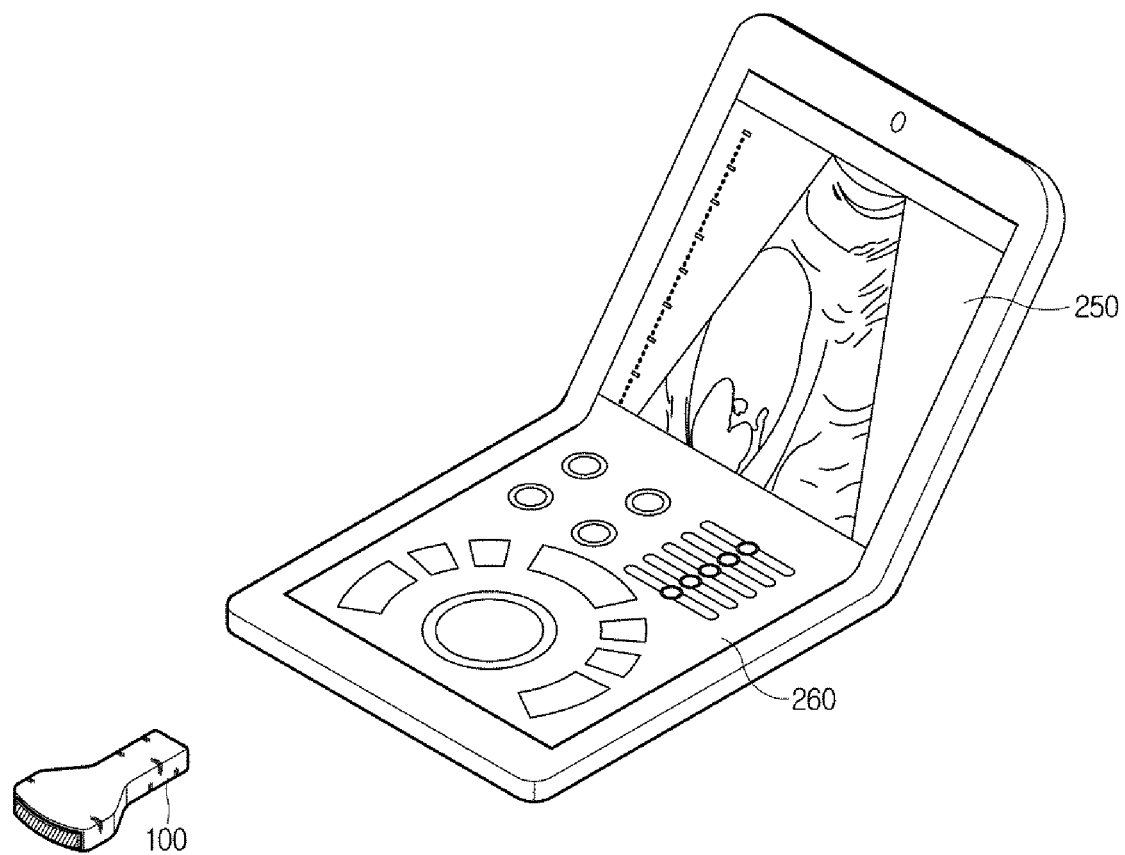

FIGS. 1A and 1B are control block diagrams illustrating the portable ultrasonic diagnostic apparatus in accordance with an exemplary embodiment. FIGS. 2 and 3 are diagrams illustrating exteriors of portable ultrasonic diagnostic apparatuses in accordance with respective other exemplary embodiments.

Referring to FIG. 1A, the portable ultrasonic diagnostic apparatus 10 includes a probe 100 which applies an ultrasonic wave to an object ob, receives an echo ultrasonic wave reflected from the object ob, and converts the echo ultrasonic wave into an electrical signal, and a main body 200 which generates an ultrasonic image based on the electrical signal.

Referring to FIG. 1B, the probe 100 in accordance with one exemplary embodiment includes a transducer module 110, a beamformer 120, a transceiving switch 123, an amplifier 124, and an analog-to-digital converter 125.

The transducer module 110 generates an ultrasonic wave according to an applied pulse and applies the ultrasonic wave to the object ob. The ultrasonic wave applied to the object ob is reflected from a target area inside the object ob. The transducer module 110 receives the reflected echo ultrasonic wave and converts the received echo ultrasonic wave into the electrical signal.

The object ob may also be a body of a human or animal, or tissue in the body such as blood vessels, bones, muscles, or the like, but is not limited thereto. Anything of which an internal structure can be imaged by the portable ultrasonic diagnostic apparatus 10 may become the object ob.

The beamformer 120 is a device which applies an appropriate delay time to the applied ultrasonic wave or the received echo ultrasonic wave so that the ultrasonic wave generated from the transducer module 110 is focused on one target area of the object ob at the same desired time or a difference between times at which the echo ultrasonic wave reflected and returned from the target area of the object ob reaches transducer elements included in the transducer module 110 is overcome.

The beamformer 120 includes a pulser 121, a pulse delay unit 122, an echo delay unit 126, and an adder 127.

The pulser 121 generates an alternating current voltage (i.e., a pulse) to drive the transducer module 110 when an ultrasonic wave is applied.

The number of pulsers 121 present correspond to the number of transducer elements included in the transducer module 110 or the number of channels.

When the ultrasonic wave is applied, the transceiving switch 123 operates in a transmission mode, the pulser 121 generates a voltage pulse, for example, in a range of −80 V to +80 V or 0 V to 200 V as a transmission pulse, and thus, the voltage pulse may be input to each of the transducer elements included in the transducer module 110.

The pulse delay unit 122 adds a delay time to a pulse according to a focus point and steering angle of the ultrasonic wave to form a transmission signal pattern when the ultrasonic wave is applied.

Further, the number of pulse delay units 122 present may correspond to the number of transducer elements included in the transducer module 110 or the number of channels.

The pulse delay unit 122 applies the delay time to each of the transducer elements so that the pulse generated from the pulser 121 may reach the focus point. In this case, the focus point is a plurality, and the plurality of focus points may form one scan line. The time delayed voltage pulse may be input to each of the transducer elements included in the transducer module 110 as a transmission pulse.

The echo delay unit 126 applies a time delay to a digital signal of each of the transducer elements according to the focus point and steering angle of the ultrasonic wave when the ultrasonic wave is received.

When the transceiving switch 123 operates in a reception mode after the ultrasonic wave application is completed and the transducer module 110 receives the echo ultrasonic wave, the echo delay unit 126 receives the digital signal corresponding to the echo ultrasonic wave from the analog-to-digital converter 125, and applies a time delay to the digital signal of each of the transducer elements included in the transducer module 110 based on the focus point and steering angle of the ultrasonic wave with respect to the target area.

As an example, the echo delay unit 126 dynamically sets a delay frequency based on at least one of whether a two-dimensional transducer array is included or not, a focusing depth, a steering angle, an aperture size, the number of activated transducer elements, and the like, and applies a delay time to the digital signal of each of the transducer elements included in the transducer module 110 according to the set delay frequency.

The adder 127 adds the time delayed digital signals of each of the transducer elements when the ultrasonic wave is received.

The adder 127 adds the digital signals of the transducer elements included in the transducer module 110 to which the delay time is applied by the echo delay unit 126 to focus into one digital signal. The focused digital signal is output from the probe 100 and transferred to a signal processing unit 220 of the main body 200. After signal processing is performed on the focused digital signal by the signal processing unit 220, various image processing methods for generating an ultrasonic image may be performed by an image processing unit 230.

In the portable ultrasonic diagnostic apparatus 10 illustrated in FIG. 1B, the beamformer 120 may be included in the probe 100 corresponding to a front-end as described above or the main body 200 corresponding to a back-end. Since an embodiment of the beamformer 120 is not limited thereto, all or some components of the beamformer 120 may be included in any one of the front-end and the back-end.

The transceiving switch 123 switches a mode to a transmission mode when the ultrasonic wave is applied or to a reception mode when the ultrasonic wave is received according to a control signal of a system controller 240 of the main body 200.

The amplifier 124 amplifies a voltage according to a current output from the transducer module 110.

The amplifier 124 may include a pre-amplifier which amplifies a fine size of an analog signal and a low noise amplifier (LNA) may be used as the pre-amplifier.

Further, the amplifier 124 may include a variable gain amplifier (VGA) (not shown) which controls a gain value according to an input signal. In this case, a time gain compensation (TGC) method which compensates a gain value according to a focus point or a distance to the focus point, or a lateral gain compensation (LGC) method which compensates a gain value in a lateral direction may be used as the VGA, however, this is not limited thereto.

The analog-to-digital converter 125 converts an analog voltage output from the amplifier 124 into a digital signal.

Although it has been described that the converted digital signal is input from the analog-to-digital converter 125 to an echo delay unit 126 of the beamformer 120 in FIG. 1B, on the other hand, it is possible that the delayed analog signal is input from the echo delay unit 126 to the analog-to-digital converter 125, and thus, the order is not limited.

Although it has been described that the analog-to-digital converter 125 is included in the probe 100 in FIG. 1B, this is not limited thereto. It is possible that the analog-to-digital converter 125 is included in the main body 200. In this case, the analog-to-digital converter 125 may receive the analog signal focused by the adder 127 from the probe 100 to convert into the digital signal.

The main body 200, which is a device including components necessary for controlling of the probe 100 or generating of the ultrasonic image based on the signal received from the probe 100, may be connected to the probe 100 through a cable or a wireless communication network.

Hereinafter, the signal processing unit 220, the image processing unit 230, and the system controller 240 included in the main body 200 will be described, and a flexible display 250 and an input unit 260 will also be described.

The signal processing unit 220 converts the focused digital signal received from the probe 100 into a form suitable for image processing. For example, the signal processing unit 220 may perform filtering for removing a noise signal except a desired frequency band.

Further, the signal processing unit 220 may be implemented using a digital signal processor (DSP), may generate ultrasonic image data by performing an envelope detection processing method which detects a size of the echo ultrasonic wave based on the focused digital signal.

The image processing unit 230 generates an image so that the user, for example, a doctor or a patient may visually determine the object ob, for example, the inside of the human body based on the ultrasonic image data generated by the signal processing unit 220.

The image processing unit 230 transmits the ultrasonic image generated using the ultrasonic image data to the flexible display 250.

Further, the image processing unit 230 may further perform additional image processing on the ultrasonic image according to the exemplary embodiments. For example, the image processing unit 230 may further perform image post-processing such as correction or readjustment of contrast, brightness, or sharpness of the ultrasonic image.

The additional image processing of the image processing unit 230 as described above may be performed according to a preset procedure, or the user's instruction or a command input through the input unit 260.

The system controller 240 controls overall operations of the portable ultrasonic diagnostic apparatus 10. For example, the system controller 240 controls operations of the signal processing unit 220, the image processing unit 230, the probe 100, and the flexible display 250.

According to the exemplary embodiment, the system controller 240 may control the operations of the portable ultrasonic diagnostic apparatus 10 according to the preset procedure, or after a predetermined control command is generated according to the user's instruction or command input through the input unit 260.

The system controller 240 may include a memory which stores program and data for controlling the probe 100 and the main body 200, and components included in the probe 100 and the main body 200, and a processor which generates a control signal according to the program and data stored in the memory.

The system controller 240 in accordance with one exemplary embodiment may change a layout of display areas displayed on the flexible display 250 when the system controller 240 receives an electrical signal from the probe 100.

The system controller 240 in accordance with another exemplary embodiment may change a layout of images displayed on the flexible display 250 when the system controller 240 receives a layout change command from the input unit 260.

When a sensor is attached to the main body 200, the system controller 240 in accordance with still another exemplary embodiment may change the layout of the images displayed on the flexible display 250 according to whether a physical deformation is caused or not or the degree of deformation detected by the attached sensor.

Detailed description of the change of the layout will be described below.

The system controller 240 may include a processor, a read only memory (ROM) which stores a control program for controlling the portable ultrasonic diagnostic apparatus 10, and a random access memory (RAM) which stores a signal input from the probe 100 or the input unit 260 of the portable ultrasonic diagnostic apparatus 10 or the ultrasonic image data and is used as a storage area corresponding to various operations performed in the portable ultrasonic diagnostic apparatus 10.

Further, a graphic processing board including the processor, the RAM, or the ROM may be included in a separate circuit board electrically connected to the system controller 240. The processor, the RAM, and the ROM may be interconnected through an internal bus.

Further, the system controller 240 may be used as a term which refers to components including the processor, the RAM, and the ROM. Further, the system controller 240 may be used as a term which refers to components including the processor, the RAM, the ROM, and the graphic processing board.

The flexible display 250, which is a display manufactured using a bendable material such as a plastic board, is referred to as a folding, rolling, or bending display which is light and unbreakable and has a flexible material compared to other displays. The flexible display 250 is freely bent and thus may also be replaced with publications for fashion for clothing as well as medical diagnosis.

Referring to FIG. 2, the flexible display 250 has a bending degree of freedom that allows the user to bend a screen. For example, the bending degree of freedom indicates that the user may hold both edges (e.g., a first end portion and a second end portion) and convexly or concavely bend back and forth.

The flexible display 250 may display various contents in one or more display areas. For example, the flexible display 250 may display the ultrasonic image generated by the image processing unit 230 in at least one of the display areas, and thus, the user may visually determine an internal structure or tissue of the object ob. Detailed description of the one or more display areas will be described below.

Referring again to FIG. 1B, the input unit 260 receives a predetermined instruction or command from the user in order to control the portable ultrasonic diagnostic apparatus 10.

For example, the input unit 260 may include a user interface such as a keyboard, a mouse, a trackball, a TGC control knob, a LGC control knob, or a paddle.

Referring to FIG. 2, the input unit 260 is implemented using the touch screen, allows the above-described trackball 261 and TGC control knobs 262 to be implemented on the flexible display 250 as the user interface. In addition, the input unit 260 allows various buttons, wheels, or knobs manipulatable by the user such as the keyboard, the mouse, the LGC control knob, or the paddle to be implemented on the flexible display 250 as the user interface.

When the input unit 260 is implemented using the touch screen, the input unit 260 is integrated with the flexible display 250 to display the contents or receive the user's command.

The input unit 260 may receive a command for simultaneously controlling the plurality of display areas as well as a command for controlling each of the plurality of display areas included in the flexible display 250.

Each of components of the probe 100 and the main body 200 may be interconnected through the bus.

Further, the probe 100 and the main body 200 may be connected through various ports and cables such as a Universal Serial Bus (USB) cable in a wire manner as illustrated in FIG. 2, or each include a wireless communication module, may be connected through a wireless communication network, and may transmit and receive an electrical signal as illustrated in FIG. 3.

Figure 4:
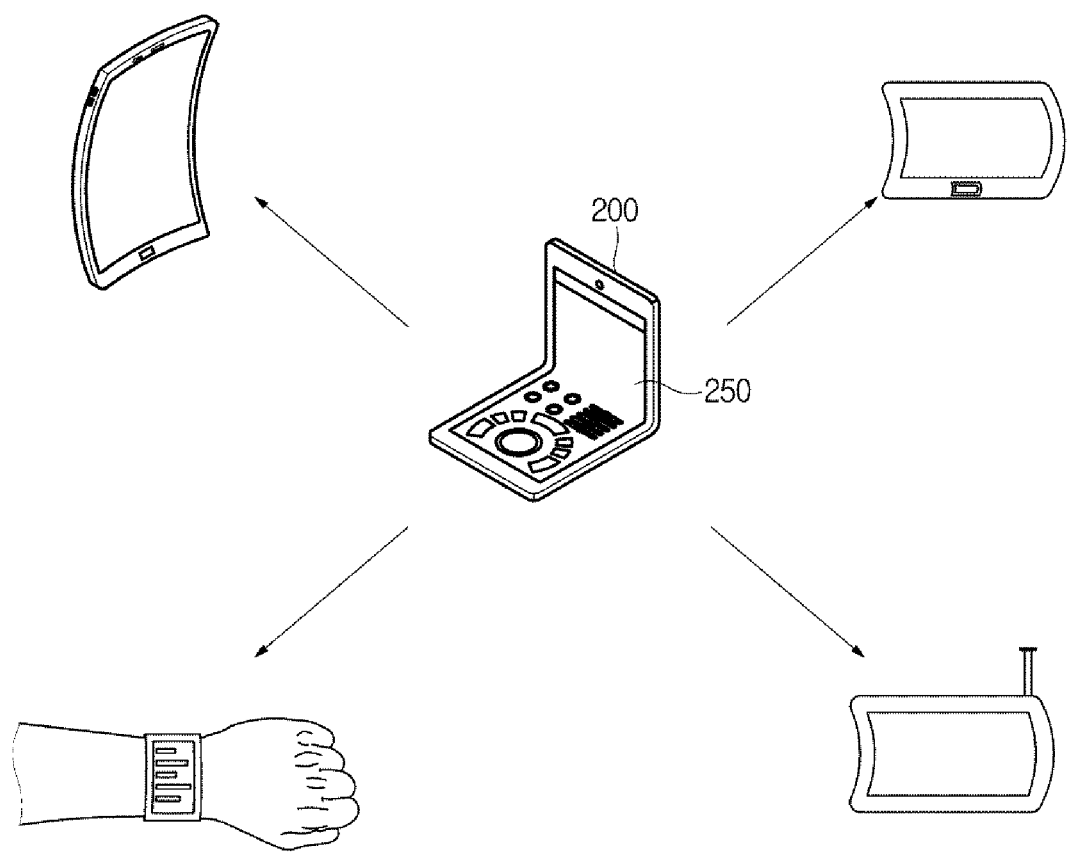
FIG. 4 is a diagram illustrating examples of various forms of a main body.

Meanwhile, although the main body 200 of a laptop form that can be folded once is described in FIGS. 2 and 3, the main body 200 may be implemented in various forms. FIG. 4 is a diagram illustrating examples of various forms of a main body.

Referring to FIG. 4, the main body 200 may be implemented using a portable computer or a portable terminal including a flexible display 250. Here, the portable computer, for example, may include a notebook computer, a laptop personal computer (PC), a tablet PC, or a slate PC, in which a web browser is installed, and the portable terminal, which is a wireless communication device that can be gripped by one hand and ensures the portability and mobility thereof, for example, may include any type of a hand-held based wireless communication device such as a personal communication system (PCS) terminal, global system for mobile communications (GSM) terminal, a personal digital cellular (PDC) terminal, a personal handy-phone system (PHS) terminal, a personal digital assistant (PDA), an international mobile telecommunication (IMT)-2000 terminal, a code division multiple access (CDMA)-2000 terminal, a wideband code division multiple access (WCDMA) terminal, a wireless broadband Internet (WiBro) terminal, a smart phone, a wearable device, etc.

The flexible display 250 included in the main body 200 may include one or more planes according to a form of the main body 200 or different from the form of the main body 200, or may include one or more concave or convex surfaces.

Hereinafter, a wireless probe which transfers digital signals to the main body 200 through a wireless communication network will be described as an example of the probe 100, and the main body 200, which includes the input unit 260 implemented on the flexible display 250 using a touch screen and is implemented in a laptop form that can be folded once, will be described as an example, but forms of the probe 100 and the main body 200 are not limited thereto.

Figure 5:
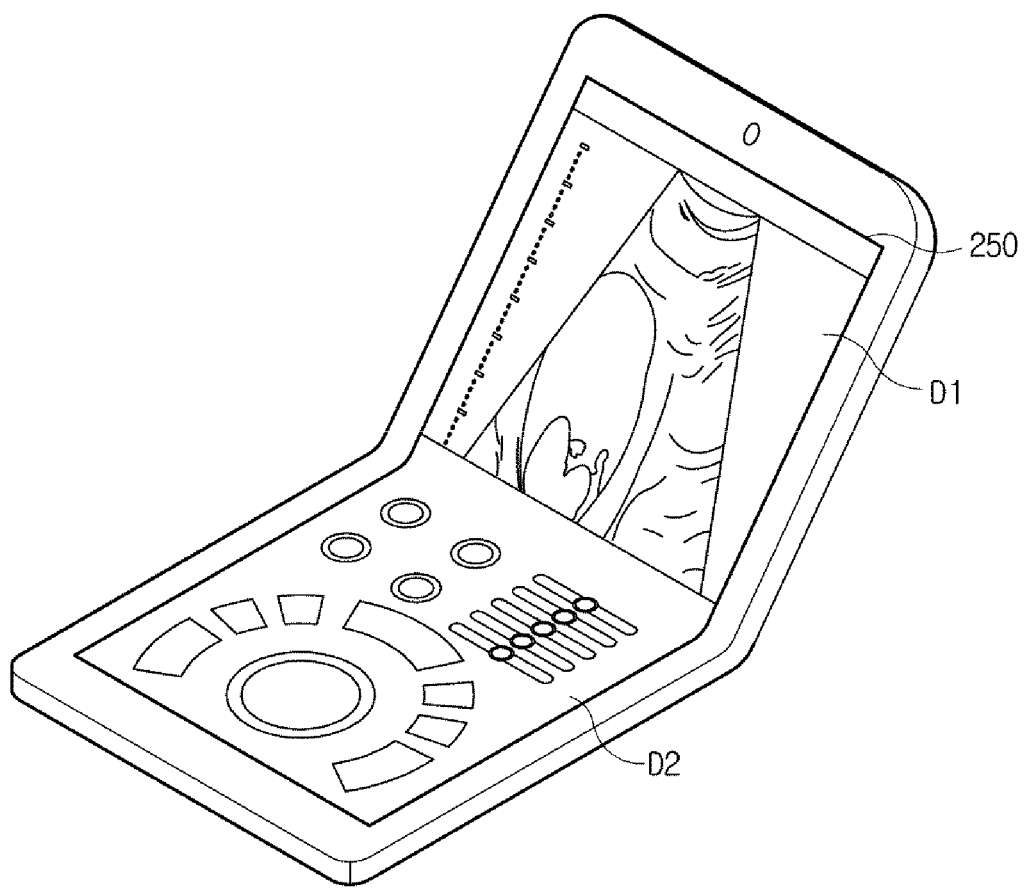
FIG. 5 is a diagram illustrating an example of one or more display areas which display contents of a flexible display.

The flexible display 250 may display contents in one or more display areas. FIG. 5 is a diagram illustrating an example of one or more display areas which display contents of a flexible display.

Here, the one or more display areas refer to unit areas of the flexible display 250 which display at least one image, and first to fourth areas to be described below refer to display areas distinct from each other.

Referring to FIG. 5, the flexible display 250 may display an ultrasonic image in a first area D1 at an upper portion thereof, and a control panel in a second area D2 at a lower portion thereof. Here, the first area D1 and the second area D2 may be implemented using a touch screen.

The ultrasonic image refers to an ultrasonic image generated by the image processing unit 230 based on the digital signals received from the probe 100, and the control panel refers to a touch screen image which receives a control command of the user.

The flexible display 250 may display the control panel in the first area D1 and the ultrasonic image in the second area D2, or the ultrasonic image or the control panel in both the first area D1 and the second area D2, and thus, the displayed image may be different from that illustrated in FIG. 5.

An example of the ultrasonic image includes an amplitude mode (A-mode) image, a brightness mode (B-mode) image, a Doppler mode (D-mode) image, an elastography mode (E-mode) image, and a motion mode (M-mode) image, or the like. Here, the D-mode image includes a color Doppler image and a spectral Doppler image.

The flexible display 250 in accordance with one exemplary embodiment may change a layout of the image displayed according to a control signal of the system controller 240.

"The change of the layout" may include extension, shrinkage, movement, rotation, or power on/off of at least one of the display areas D1 and D2, and enlargement, reduction, rotation, or change of the image displayed in at least one of the display areas D1 and D2.

FIGS. 6 to 12 are diagrams illustrating various examples of a flexible display of which a layout is changed according to a control signal of a system controller.

Referring to FIG. 6, the flexible display 250 may extend the first area D1 according to the control signal. In this case, an area of the first area D1 in which the ultrasonic image is displayed may extend to an area of the second area D2, and the second area D2 may be shrunk by the extension of the first area D1. On the other hand, the flexible display 250 may shrink the first area D1 and extend the second area D2 according to the control signal.

Here, the extension includes at least one of extension in a longitudinal direction, a horizontal direction, and a diagonal direction.

When the first area D1 is extended, a range of the ultrasonic image of the object ob displayed in the first area D1 may be widened, and when the second area D2 is shrunk, a command which the control panel displayed in the second area D2 may receive may be changed.

For example, when the main body 200 receives the digital signal from the probe 100, the first area D1 may be extended in a longitudinal direction, the second area D2 may be shrunk in a longitudinal direction, the control panel displayed in the second area D2 may be changed from a state in which the TGC control knobs 262 and the trackball 261 are displayed to a state in which only the trackball 261 is displayed.

Further, referring to FIG. 7, the flexible display 250 may extend the first area D1 and rotate the image displayed in the first area D1 according to the control signal. In this case, the area of the first area D1 in which the ultrasonic image is displayed may extend into the area of the second area D2, the ultrasonic image may be rotated by a predetermined angle, and the second area D2 may be removed by the extension of the first area D1. On the other hand, the flexible display 250 may remove the first area D1, extend the second area D2, and rotate the image displayed in the second area D2 according to the control signal.

When the first area D1 extends and rotates, the range of the ultrasonic image of the object ob displayed in the first area D1 may be increased.

For example, when the main body 200 receives the digital signal from the probe 100, the first area D1 may rotate by 90° and simultaneously extend in a horizontal direction, and the second area D2 may be removed.

An angle of rotation or a degree of extension may be arbitrarily changed by the user through operations of the control panel or a separate input device.

Further, referring to FIG. 8, the flexible display 250 may move each of areas in which the ultrasonic image and the control panel are displayed according to the control signal.

In this case, the flexible display 250 may move the ultrasonic image displayed in the first area D1 to the second area D2, and the control panel displayed in the second area D2 to the first area D1 according to the control signal.

For example, when the main body 200 receives the digital signal from the probe 100, the ultrasonic image displayed in the first area D1 may be displayed in the second area D2 and the control panel displayed in the second area D2 may be displayed in the first area D1.

Figure 9:
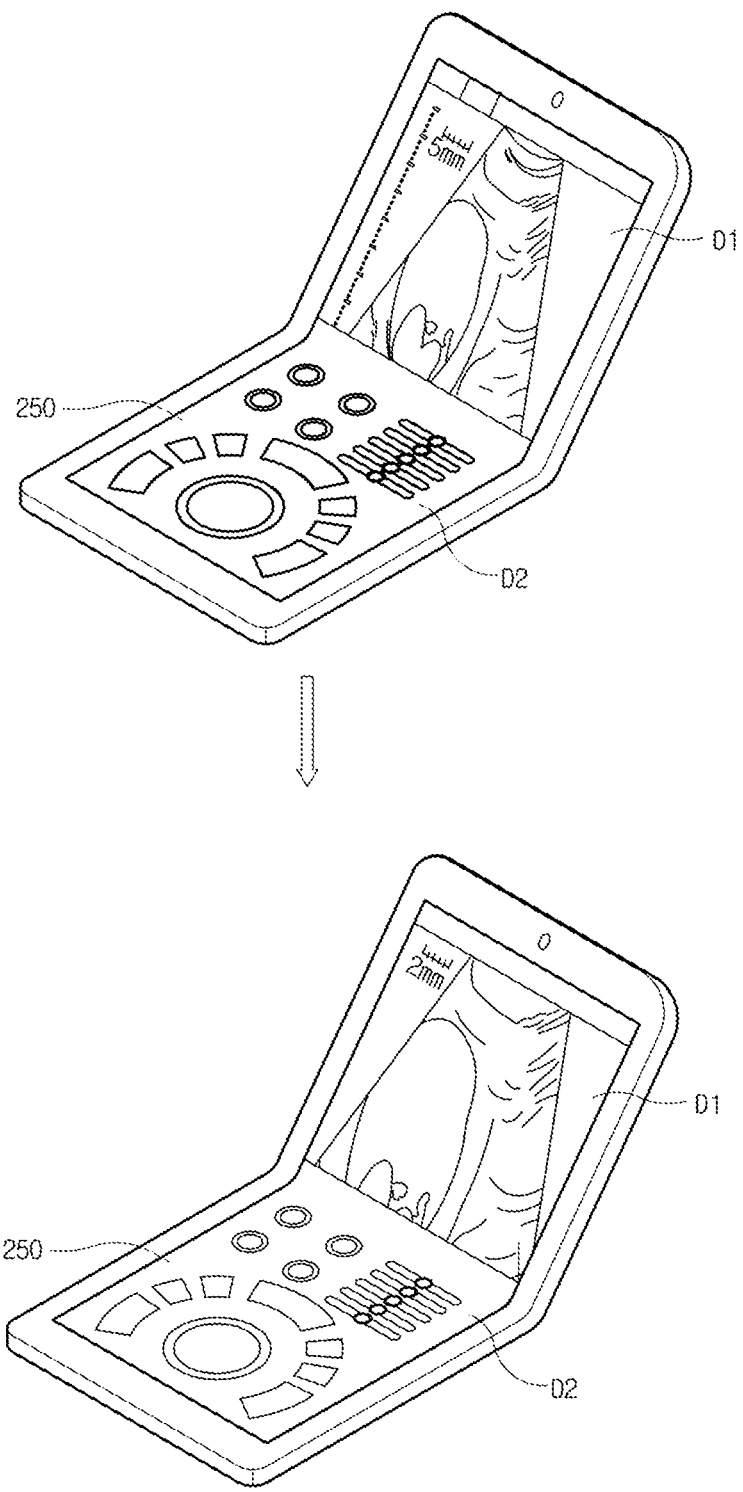

Further, referring to FIG. 9, the flexible display 250 may enlarge or reduce the image displayed in the first area D1 or the second area D2 according to the control signal.

For example, when the main body 200 receives the digital signal from the probe 100, the flexible display 250 may increase the scale of the ultrasonic image displayed in the first area D1 to enlarge the ultrasonic image. In this case, an enlargement center point of the enlarged ultrasonic image may be a predetermined point, the scale of enlargement or a movement of the enlargement center point may be operated by the user through the control panel or a separate input device.

Figure 10:
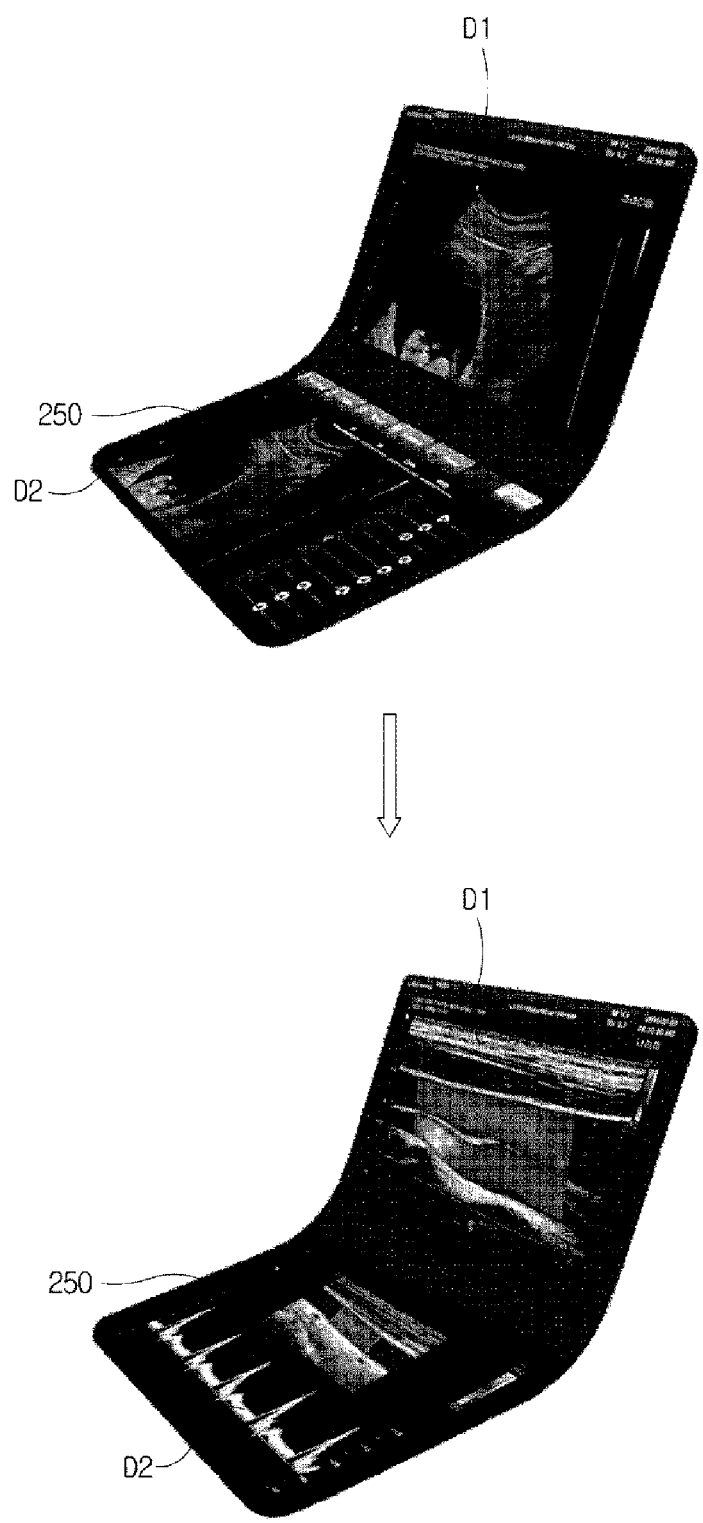

Further, referring to FIGS. 10 to 12, the flexible display 250 may change the image displayed in the first area D1 or the second area D2 according to the control signal.

For example, referring to FIG. 10, in a state in which the flexible display 250 displays a B-mode image in the first area D1 and the B-mode image and a TGC control knob are simultaneously displayed in the second area D2, when the main body 200 receives a digital signal related to a D-mode image from the probe 100, the flexible display 250 displays a color Doppler image in the first area D1, and a spectral Doppler image in the second area D2.

Further, referring to FIG. 11, in a state in which the flexible display 250 displays a B-mode image in the first area D1 and a first control panel which displays a trackball 261 and TGC control knobs 262 are displayed in the second area D2, when the flexible display 250 receives a command (e.g., pressing separate touch buttons 263) which changes the image displayed in the first area D1 to a second control panel due to the first control panel, the flexible display 250 may display LGC control knobs 264 and a sub display area 265 in the first area D1, and the first control panel in the second area D2.

Further, referring to FIG. 12, in a state in which the flexible display 250 displays a B-mode image in the first area D1 and the first control panel which displays the trackball 261 and the TGC control knobs 262 are displayed in the second area D2, when the flexible display 250 receives a command (e.g., pressing separate touch buttons 266) which changes the image displayed in the second area D2 to a third control panel due to the first control panel, the flexible display 250 may display the ultrasonic image in the first area D1, and the third control panel which receives a user input through a keyboard in the second area D2.

In addition, the flexible display 250 may display various images in the first area D1 or the second area D2 according to the control signal, and thus, it is not limited to the change to the color Doppler image and the spectral Doppler image illustrated in FIG. 10, to the change from the ultrasonic image in the first area D1 to the control panel illustrated in FIG. 11, and to the change to a mode of the control panel in the second area D2 illustrated in FIG. 12.

Meanwhile, the flexible display 250 displays the image in at least one of the display areas according to the control signal of the system controller 240 and changes a layout of the image, and thus, the control signal may be differently generated according to the transmitting of the electrical signal of the probe 100, the user input, or a detection signal of a separately mounted sensor.

According to one exemplary embodiment, when the system controller 240 receives the electrical signals from the probe 100, the system controller 240 may generate the control signal which changes the layout of the image displayed in at least one of the display areas.

For example, when the probe 100 and the main body 200 are connected through a USB cable, the USB cable is connected to a USB port of the main body 200, and when the USB cable is connected to the USB port of the main body 200, the system controller 240 may generate the control signal which extends the first area D1.

Further, in the case in which the probe 100 and the main body 200 are connected through a wireless communication network, when it is determined that the main body 200 and the probe 100 are connectable within a distance through the wireless communication network, the system controller 240 may generate the control signal which extends the first area D1.

According to another exemplary embodiment, when the system controller 240 receives a preset command from the user, the system controller 240 may generate the control signal which changes the layout of the image displayed in at least one of the display areas.

For example, when a separate "emergency mode" button is provided in the main body 200 and the emergency mode button is pressed, the system controller 240 enters in the "emergency mode," and may generate the control signal so that the flexible display 250 which displays the ultrasonic image in one area displays the ultrasonic image and the control panel in the first area D1 and the second area D2, respectively, in multiple areas.

Further, when the user presses the emergency mode button, the system controller 240 enters in the emergency mode, and may generate the control signal so that the flexible display 250 displays an emergency mode image in the first area D1 and the ultrasonic image in the second area D2. Here, the entry to the emergency mode refers to executing a program which guides a portion necessary for ultrasonic diagnosis using at least one of an image, a sound, and a text when an emergency occurs.

Hereinafter, a portable ultrasonic diagnostic apparatus which guides a portion necessary for the ultrasonic diagnosis to the user through an image will be described with reference to FIGS. 13 to 18.

Figure 17:
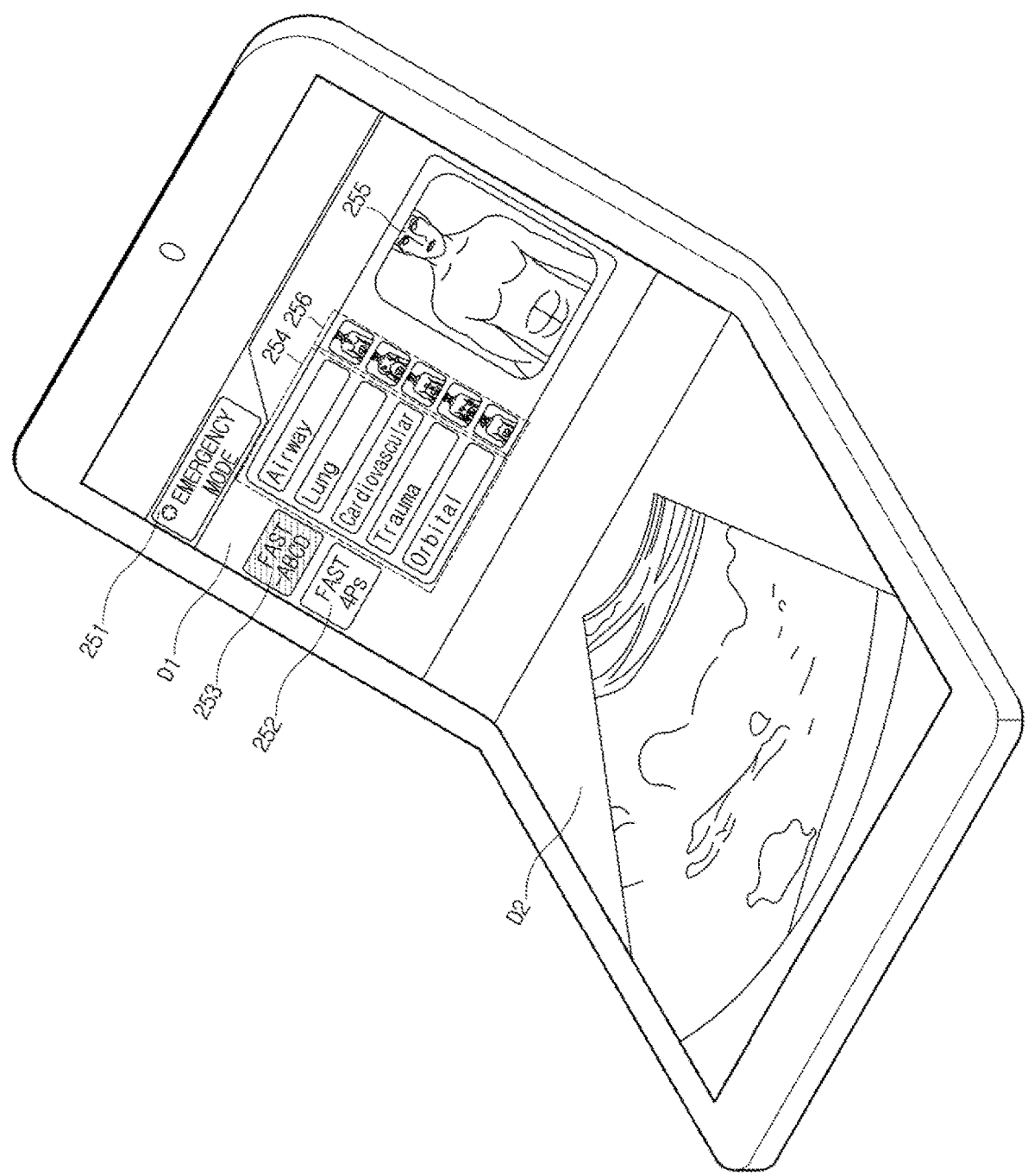
FIGS. 17 and 18 are diagrams illustrating examples of an image displayed on a flexible display which guides diagnosis to the user according to a second reference.
Figure 18:
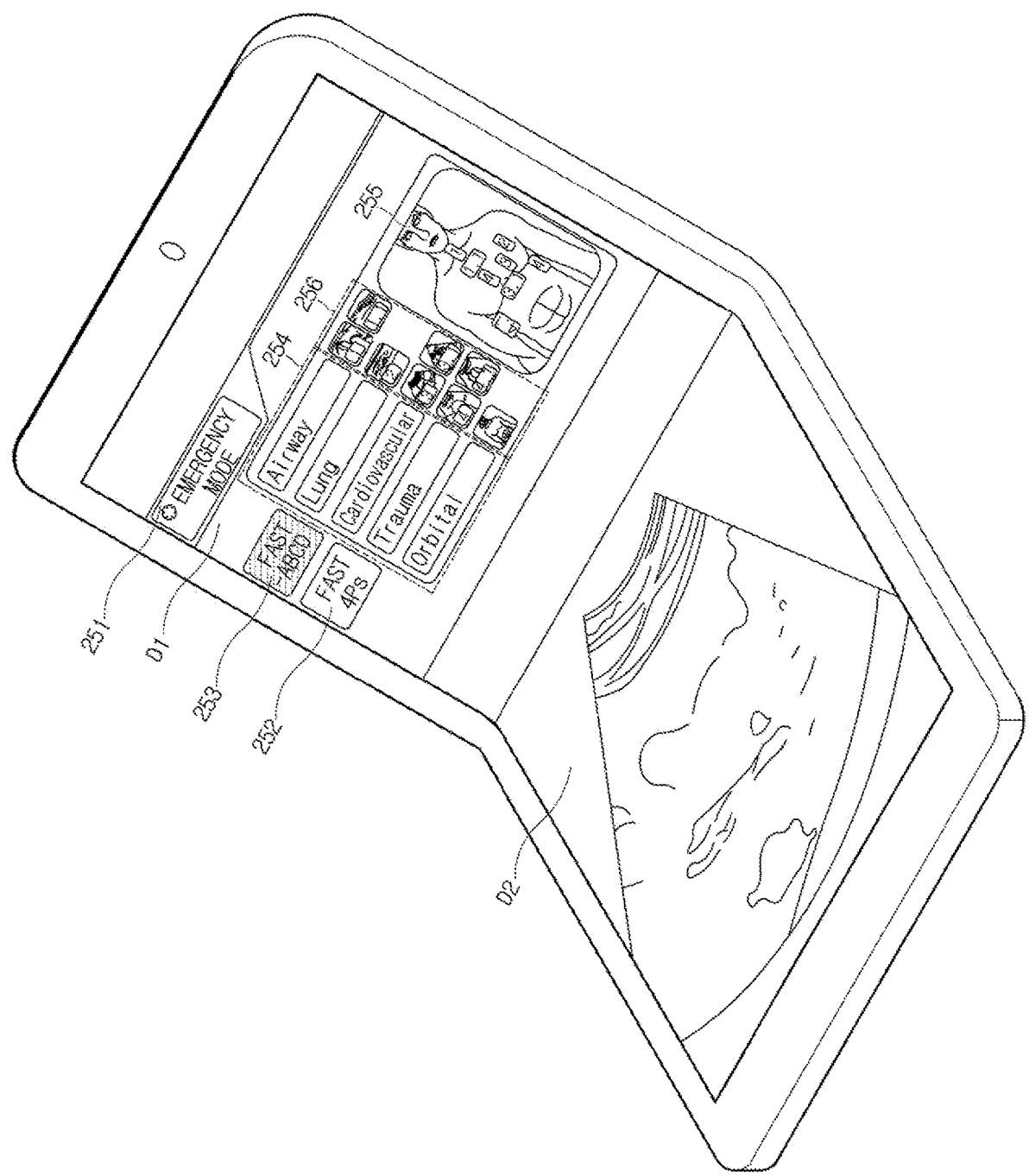

FIGS. 13 to 16 are diagrams illustrating examples of an image displayed on a flexible display which guides diagnosis to the user according to a first reference. FIGS. 17 and 18 are diagrams illustrating examples of an image displayed on a flexible display which guides diagnosis to the user according to a second reference.

The first reference, for example, may be a focused assessment with sonography for trauma (FAST) pericardial, perihepatic, perisplenic, and pelvic (4Ps) reference as an international reference, and the second reference, for example, may be a FAST airway, breathing, circulation, and disability (ABCD) reference as an international reference. Hereinafter, the first reference will be described as the FAST 4Ps reference, and the second reference will be described as the FAST ABCD reference.

Figure 13:
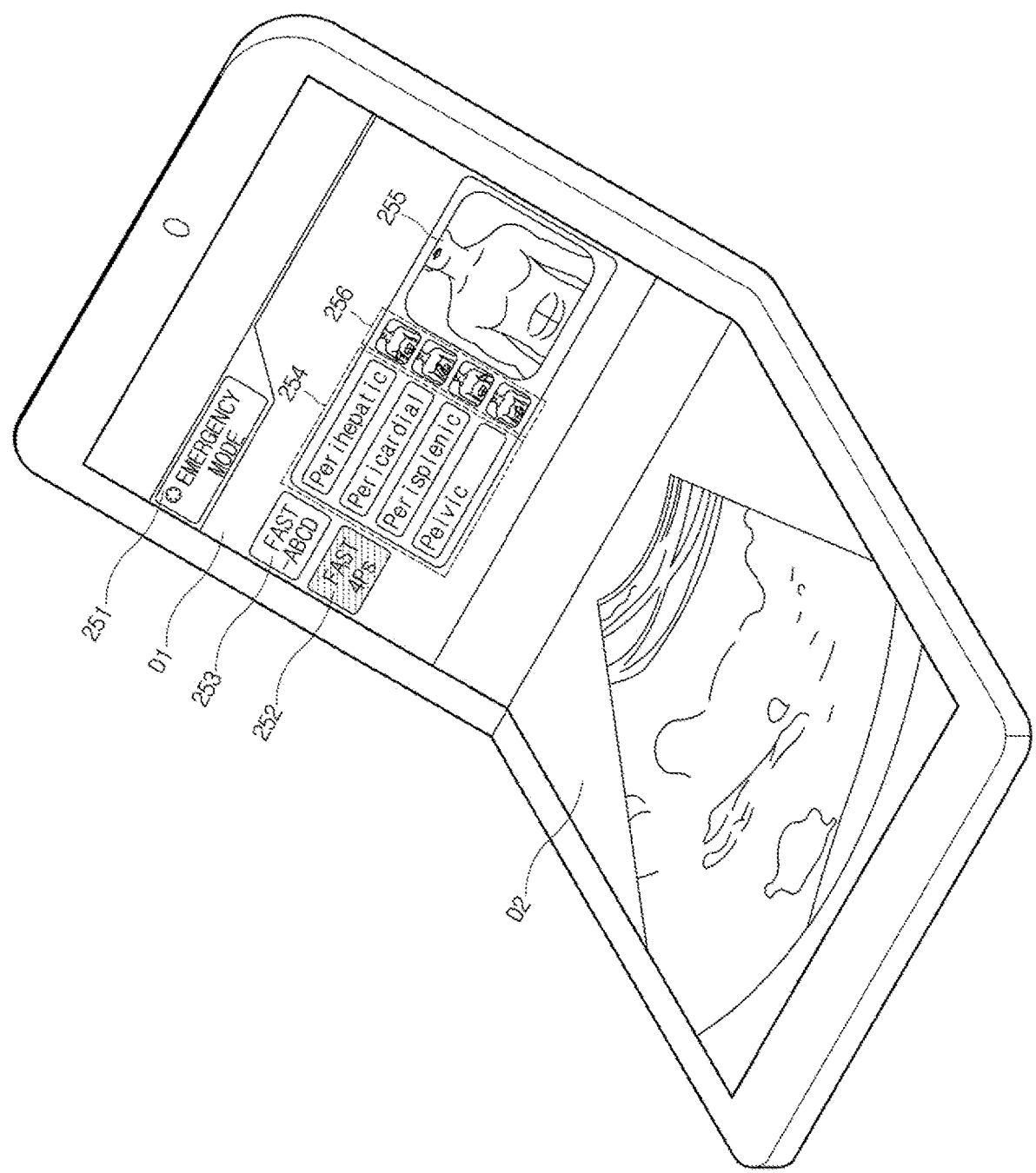
FIGS. 13 to 16 are diagrams illustrating examples of an image displayed on a flexible display which guides diagnosis to the user according to a first reference.

Referring to FIG. 13, when an emergency mode button or an emergency mode icon 251 is selected by the user, a first reference icon 252 and a second reference icon 253 may be displayed in a first area D1 of the flexible display.

When the user selects any one of the first and second reference icons 252 and 253, one or more diagnosis portions which can be diagnosed may be displayed in a diagnosis portion display area 254 of the first area D1 according to the selected reference, and when the user selects any one of the diagnosis portions, the selected diagnosis portion may be displayed in a guide area 255 of the first area D1.

Furthermore, a position of each of the diagnosis portions may be briefly displayed as a thumbnail in a thumbnail display area 256.

Figure 14:
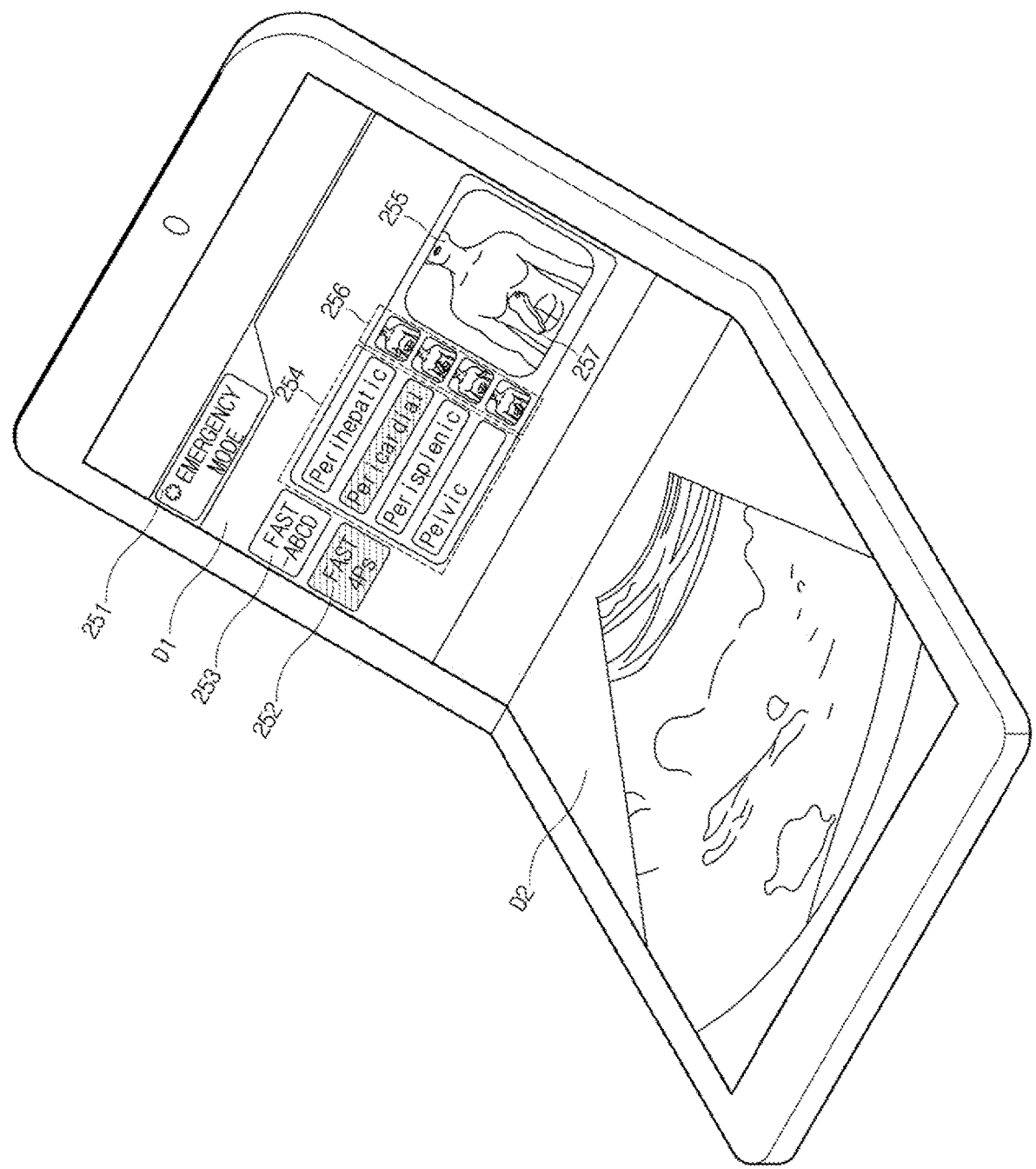

For example, referring to FIG. 14, when the first reference icon 252 is selected, an icon for selecting any one of perihepatic, pericardial, perisplenic, and pelvic portions may be displayed in a diagnosis portion display area 254.

When the user selects the pericardial portion, a position and direction of a virtual probe 257 for obtaining an image of the pericardial portion may be displayed in the guide area 255. In this case, the user may actually locate the probe 100 at the pericardial portion of the object ob with reference to the guide area 255, and an ultrasonic image of the pericardial portion may be displayed in the second area D2 by transmission and reception of an ultrasonic wave. The ultrasonic image of the pericardial portion may be stored in a memory.

Figure 15:
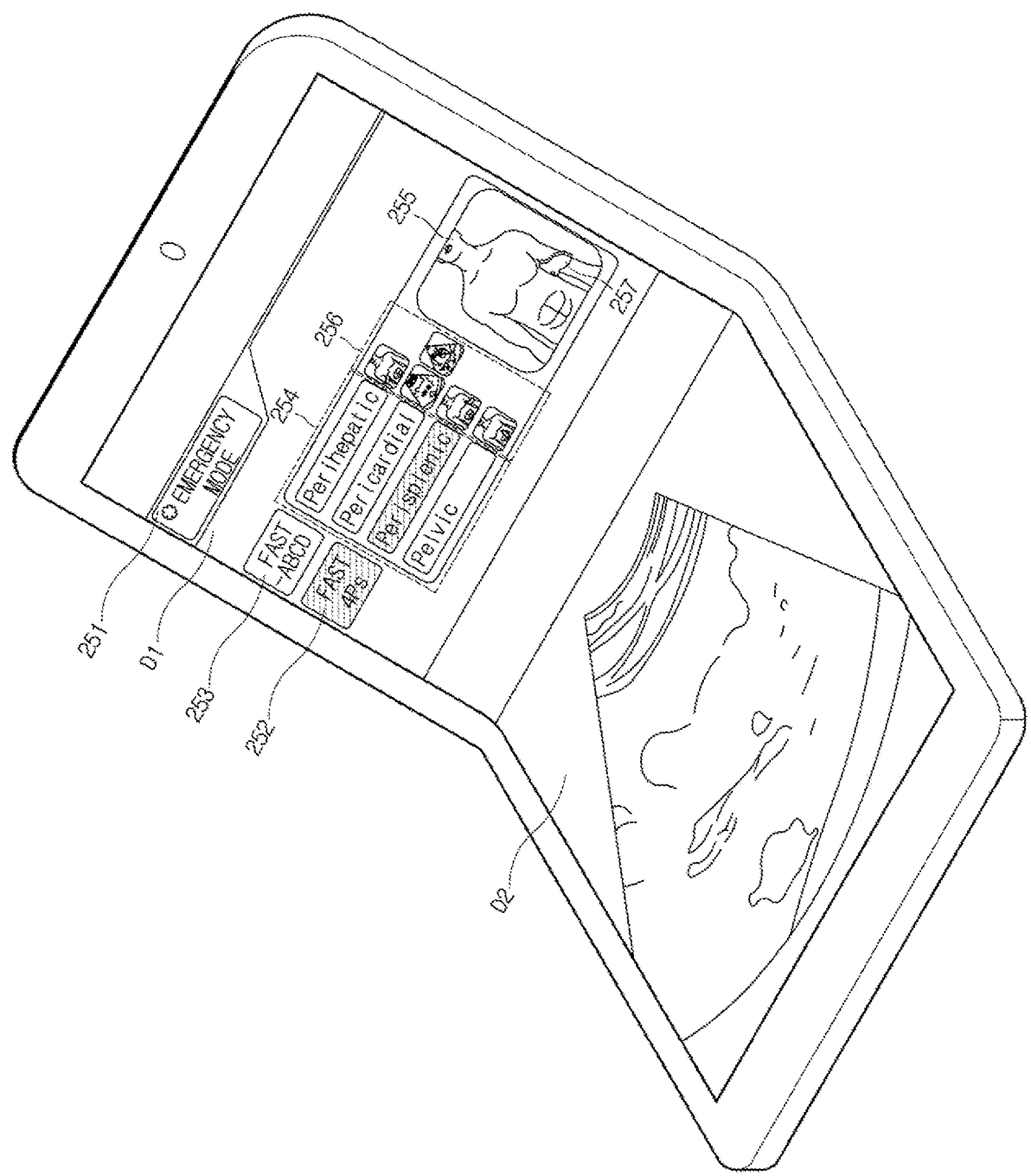

Further, referring to FIG. 15, when an ultrasonic image of the pericardial portion is obtained, a thumbnail of a position of a diagnosis portion displayed in a thumbnail display area 256 may be changed to a thumbnail of the obtained ultrasonic image.

Thus, the user may determine that the ultrasonic image is already obtained for any diagnosis portion.

Figure 16:
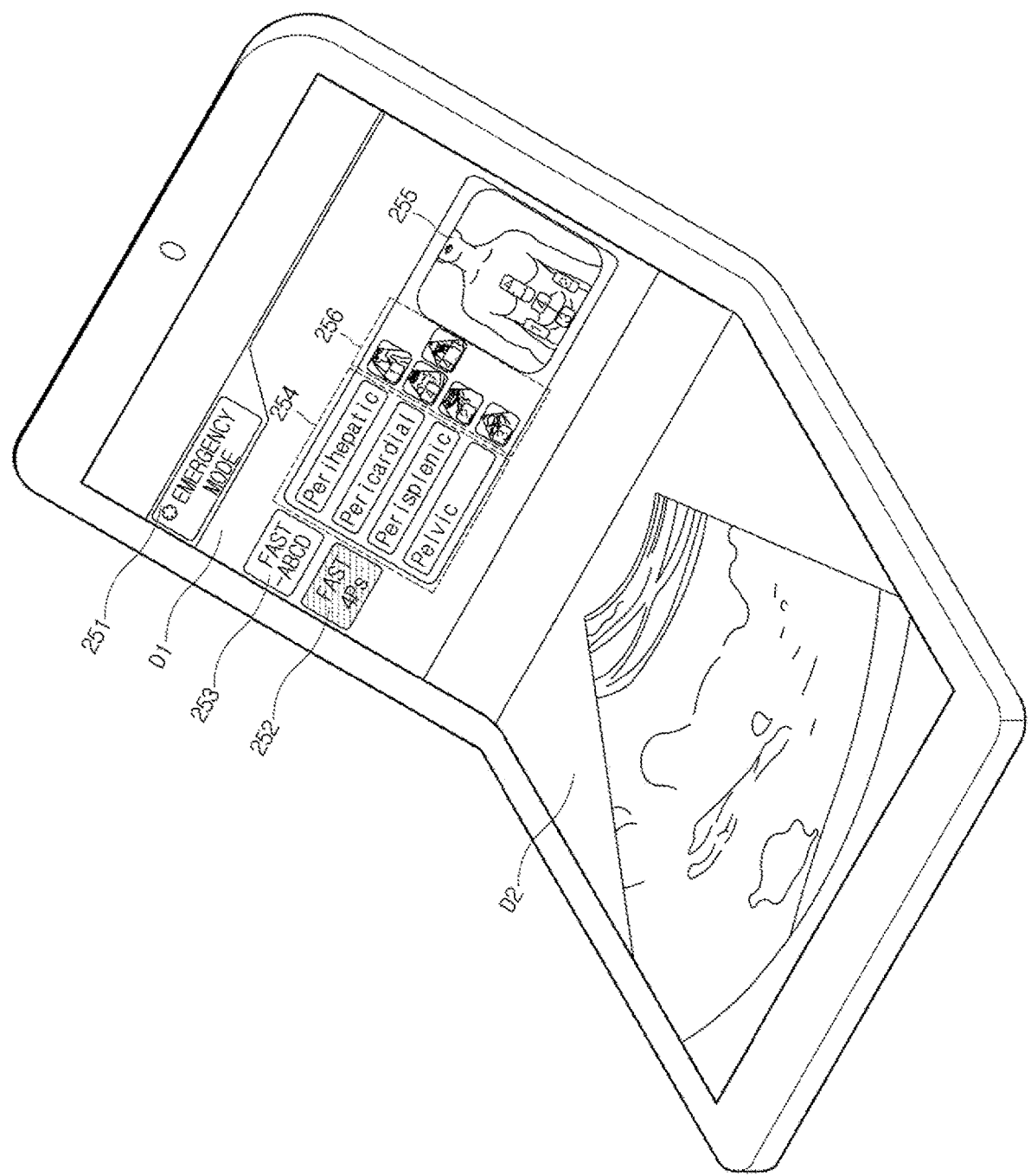

Further, referring to FIG. 16, when an ultrasonic image of each of the diagnosis portions is obtained, thumbnail indicators of the ultrasonic image displayed in the thumbnail display area 256 may be further displayed in the guide area 255.

For example, when an ultrasonic image of the perihepatic portion is obtained and a thumbnail of the ultrasonic image is displayed as a first thumbnail, a first indicator may be displayed at a point at which the perihepatic portion is located in the guide area 255.

Further, when any ultrasonic image of two pericardial portions is obtained and a thumbnail of each ultrasonic image is displayed as a fourth thumbnail and a 4.1 thumbnail, a fourth indicator and a 4.1 indicator may be displayed at points at which the pericardial portions are located in the guide area 255.

Further, when an ultrasonic image of the perisplenic portion is obtained and a thumbnail of the ultrasonic image of the perisplenic portion is displayed as a second thumbnail, a second indicator may be displayed at a point at which the perisplenic portion is located in the guide area 255.

When an ultrasonic image of the pelvic portion is obtained and a thumbnail of the ultrasonic image of the pelvic portion is displayed as a third thumbnail, a third indicator may be displayed at a point at which the pelvic portion is located in the guide area 255.

Meanwhile, referring to FIG. 17, when the second reference icon 253 is selected, icons for respectively selecting any one diagnosis portion of an airway, lung, cardiovascular, trauma, and orbital portions may be displayed in the diagnosis portion display area 254.

Similar to the first reference, when the user selects the airway portion, a position and direction of the virtual probe for obtaining an image of the airway portion may be displayed in the guide area 255. In this case, the user may actually locate the probe 100 at the airway portion of the object ob with reference to the guide area 255, and an ultrasonic image of the airway portion may be displayed in the second area D2 by transmission and reception of the ultrasonic wave. The ultrasonic image of the airway portion may be stored in a memory.

Further, in the same manner as the first reference, when the ultrasonic image of the airway portion is obtained, a thumbnail of a position of a diagnosis portion displayed in the thumbnail display area 256 may be changed to a thumbnail of the obtained ultrasonic image.

Thus, the user may determine that the ultrasonic image is already obtained for any diagnosis portion.

Further, referring to FIG. 18, in the same manner as the first reference, when the ultrasonic image of each of the diagnosis portions is obtained, a thumbnail indicator of the ultrasonic image displayed in the thumbnail display area 256 may be further displayed in the guide area 255.

For example, when the ultrasonic image of the airway portion is obtained and the thumbnail of the ultrasonic image is displayed as a first thumbnail, a first indicator may be displayed at a point at which the airway portion is located in the guide area 255.

Further, when an ultrasonic image of the lung portion is obtained and a thumbnail of the ultrasonic image of the lung portion is displayed as a second thumbnail, a second indicator may be displayed at a point at which the lung portion is located in the guide area 255.

Further, when an ultrasonic image of the cardiovascular portion is obtained and thumbnails of ultrasonic images of the cardiovascular portion are displayed as a third thumbnail and a 3.1 thumbnail, a third indicator and a 3.1 indicator may be displayed at points at which the cardiovascular portion is located in the guide area 255.

When ultrasonic images of the trauma portions are obtained and thumbnails of the ultrasonic images of the trauma portions are displayed as a fourth thumbnail and a 4.1 thumbnail, a fourth indicator and a 4.1 indicator may be displayed at points at which the trauma portions are located in the guide area 255.

Although it has been described that the emergency mode image is displayed in the first area D1 and the ultrasonic image is displayed in the second area D2 in the above described example, the display areas of the emergency mode image and the ultrasonic image are not limited thereto, and disposition thereof may be interchanged or the display areas may also be displayed in the other area. Further, the control panel may be displayed in the second area D2 in addition to the ultrasonic image, however, it is not limited to that the ultrasonic image is displayed.

Further, although it has been described that each reference, diagnosis portion, or the like is selected by icon selection of the user in the above described example, a next reference or diagnosis portion may be automatically selected by the system controller 240 when the ultrasonic image of each reference or diagnosis portion is obtained.

Further, a selectable diagnosis portion may be changed or added according to the user input. Further, when the control panel displayed in the second area D2 of the flexible display 250 includes a freeze button which stops the ultrasonic image and the user touches and inputs the freeze button, the system controller 240 may generate a control signal so that the flexible display 250, which displays the image in the plurality of display areas in multiple areas, displays only in the first area D1 and removes the second area D2. In this case, the ultrasonic image displayed in the first area D1 of the flexible display 250 may be stopped by the input of the freeze button even when the electrical signal is continuously transmitted from the probe 100.

According to still another exemplary embodiment, the system controller 240 may generate a control signal which changes a layout of at least one of the display areas according to a detection signal of a separately mounted sensor. Hereinafter, a process of generating the control signal of the main body 200 on which the sensor is mounted will be described with reference to FIGS. 19 to 23.

Figure 19:
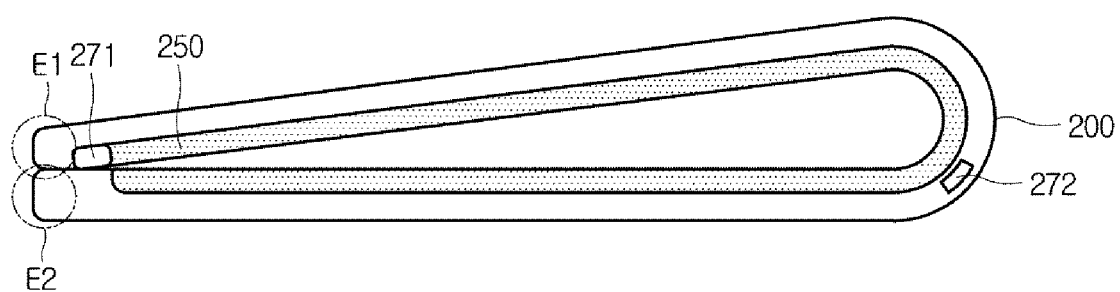
FIG. 19 is a diagram illustrating an exterior of a main body on which a sensor is mounted in accordance with another exemplary embodiment.
Figure 20:
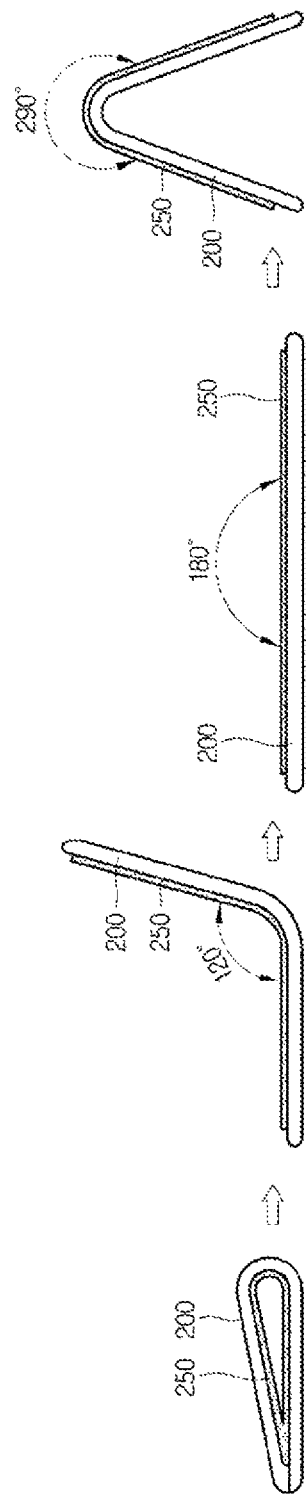
FIG. 20 is a diagram for describing examples of various forms of a flexible display.
Figure 21:
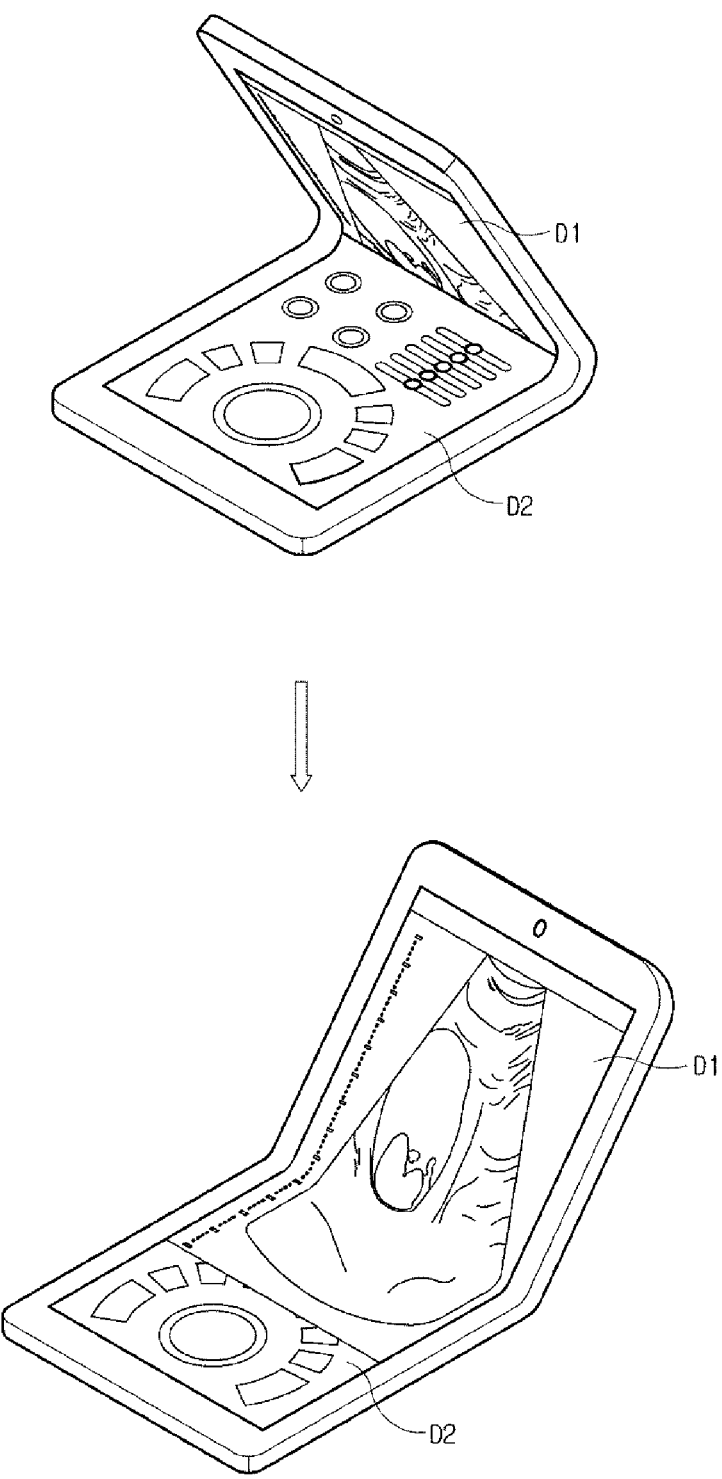
Figure 22:
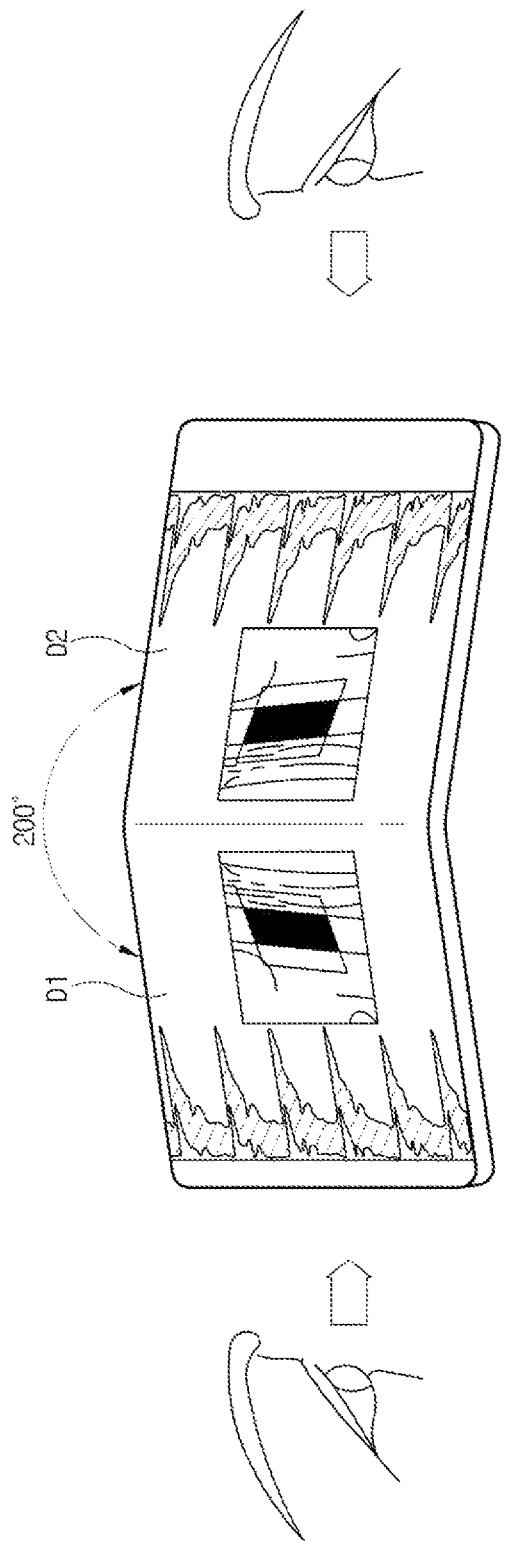

FIG. 19 is a diagram illustrating an exterior of a main body on which a sensor is mounted in accordance with another exemplary embodiment. FIG. 20 is a diagram for describing examples of various forms of a flexible display. FIGS. 21 to 23 are diagrams for describing examples of a flexible display of which a layout is changed according to a control signal The flexible display 250 included in a main body 200 uses a bendable material as described above and has a folding, rolling, or bending property.

In order to determine a degree to which the flexible display 250 is folded or curled, the main body 200 may further include separate sensors 271 and 272.

For example, when the flexible display 250 having a first end portion E1 and a second end portion E2 is bent in any one direction as illustrated in FIG. 19, a contact sensor 271 of the main body 200 detects whether the first end portion E1 and the second end portion E2 are in contact with each other or not, and thus may determine whether the flexible display 250 is folded or not.

When the contact sensor 271 detects the contact of the first end portion E1 and the second end portion E2, the system controller 240 may change a layout of the flexible display 250 based on a detection signal of the contact sensor 271.

Further, when the flexible display 250 is bent in any one direction, the other (angle) sensor 272 of the main body 200 detects a separating or facing degree of the first end portion E1 and the second end portion E2, and thus may determine a bending degree of the flexible display 250.

When the angle sensor 272 detects the bending degree of the flexible display 250, the system controller 240 may change the layout of the flexible display 250 based on a detection signal of the angle sensor 272.

Referring to FIG. 20, when the contact sensor 271 detects the contact of the first end portion E1 and the second end portion E2 and the angle sensor 272 determines an angle between the first end portion E1 and the second end portion E2 to be less than 30°, the system controller 240 may control so that the image is not displayed in each area of the flexible display 250.

Next, when the contact sensor 271 detects the non-contact between the first end portion E1 and the second end portion E2 and the angle sensor 272 determines the angle between the first end portion E1 and the second end portion E2 to be 30° or more and less than 130°, the system controller 240 may control so that a predetermined image is displayed in each area of the flexible display 250.

Next, when the contact sensor 271 detects the non-contact between the first end portion E1 and the second end portion E2 and the angle sensor 272 determines the angle between the first end portion E1 and the second end portion E2 to be 130° or more and less than 190°, the system controller 240 may control so that any one area of the flexible display 250 is extended and the other areas are shrunk.

For example, referring to FIG. 21, when the flexible display 250 is changed from a folding state to a unfolded state by the manipulation of the user, the contact sensor 271 detects the non-contact between the first end portion E1 and the second end portion E2, and the angle sensor 272 determines the angle between the first end portion E1 and the second end portion E2 to be 130° or more, the system controller 240 may extend an area of the first area D1 and shrink an area of the second area D2 so as to be in proportional to the angle between the first end portion E1 and the second end portion E2.

Referring again to FIG. 20, when the contact sensor 271 detects the non-contact between the first end portion E1 and the second end portion E2 and the angle sensor 272 determines the angle between the first end portion E1 and the second end portion E2 to be 190° or more and less than 360°, the system controller 240 may control so that the same plane of the same image is displayed or a front/rear ultrasonic image of the three dimensional object ob, a left/right ultrasonic image, or a current/past ultrasonic image is displayed in each area of the flexible display 250.

For example, referring to FIG. 22, when the flexible display 250 is unfolded in a different direction from the folded direction by the operation of the user and the angle sensor 272 determines the angle between the first end portion E1 and the second end portion E2 to be 200°, the system controller 240 may control the flexible display 250 so that the same ultrasonic image is displayed in the first area D1 and the second area D2. In this case, a user which observes the first area D1 and a user which observes the second area D2 may observe the same ultrasonic image.

Further, referring to FIG. 23, when the flexible display 250 is unfolded in a different direction from the folded direction by the operation of the user and the angle sensor 272 determines the angle between the first end portion E1 and the second end portion E2 to be 200°, the system controller 240 may control the flexible display 250 so that the front of the three-dimensional image is displayed in the first area D1 and the rear of the three-dimensional image is displayed in the second area D2. In this case, the user may simultaneously observe the front and rear of the three-dimensional image on one flexible display 250.

As described above, although the system controller 240 may change the layout of the flexible display 250 based on the detection signals of the contact sensor 271 and the angle sensor 272, the sensors included in the main body 200 are not limited to the contact sensor 271 and the angle sensor 272 and include various sensors capable of detecting a physical change of the flexible display 250 such as a gyro sensor, an acceleration sensor, a pressure sensor, a temperature sensor, a deformation sensor, etc.

Further, the layout of the flexible display 250 changed by the detection signals of the sensors is not limited to the above described.

Meanwhile, although the flexible display 250 which is folded once and displays one image in each area and the main body 200 including the same have been described in the above-described embodiment, the flexible display 250 may be folded multiple times and may display the plurality of images in each area.

Figure 24A:
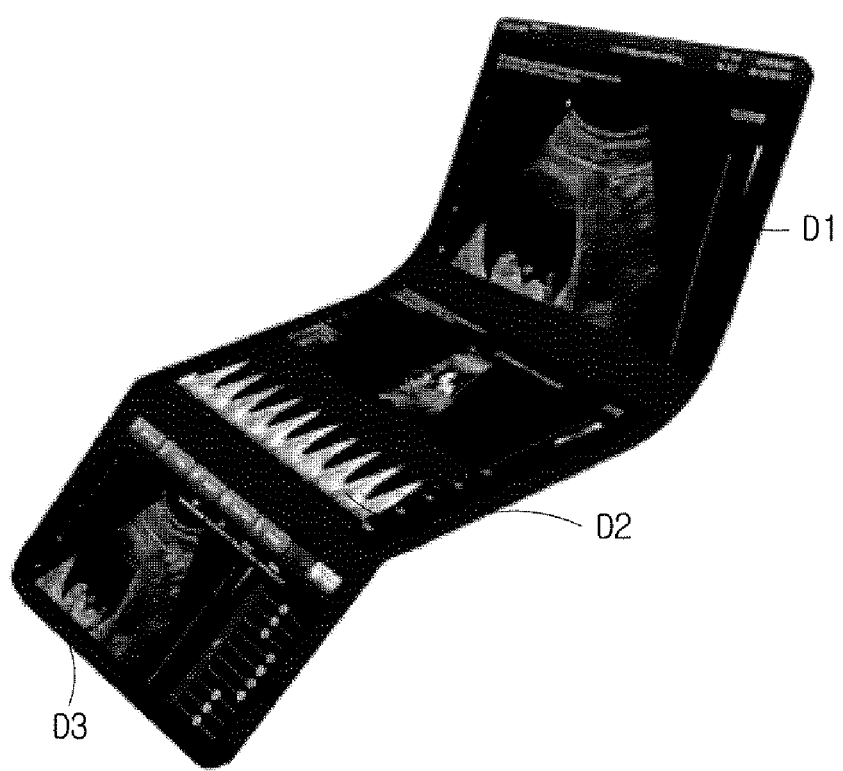
FIGS. 24A and 24B are diagrams illustrating exteriors of main bodies including flexible displays which are folded two and three times, respectively.
Figure 24B:
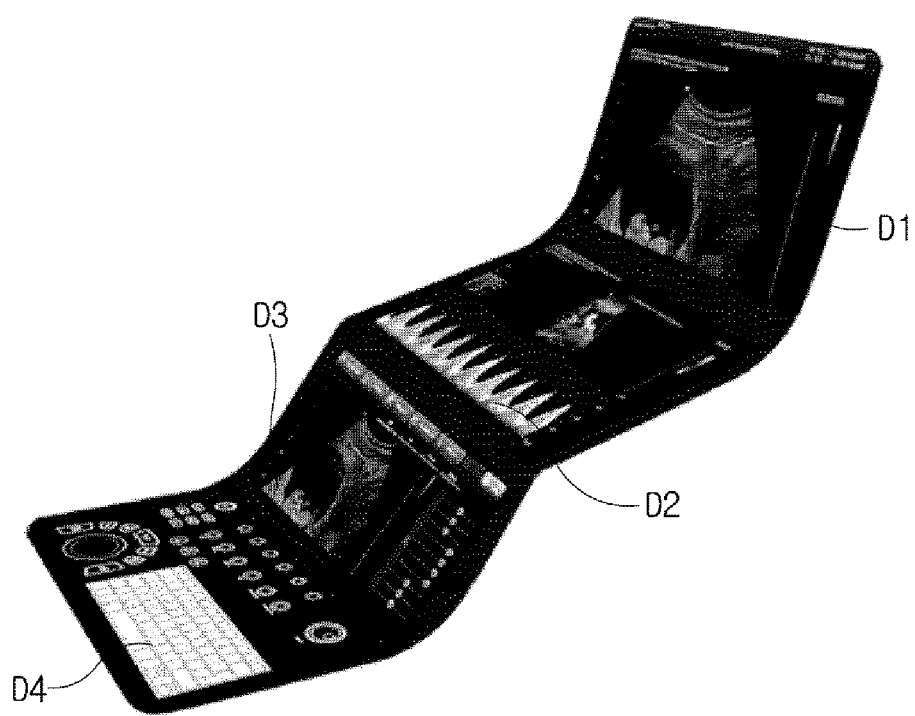
Figure 24C:
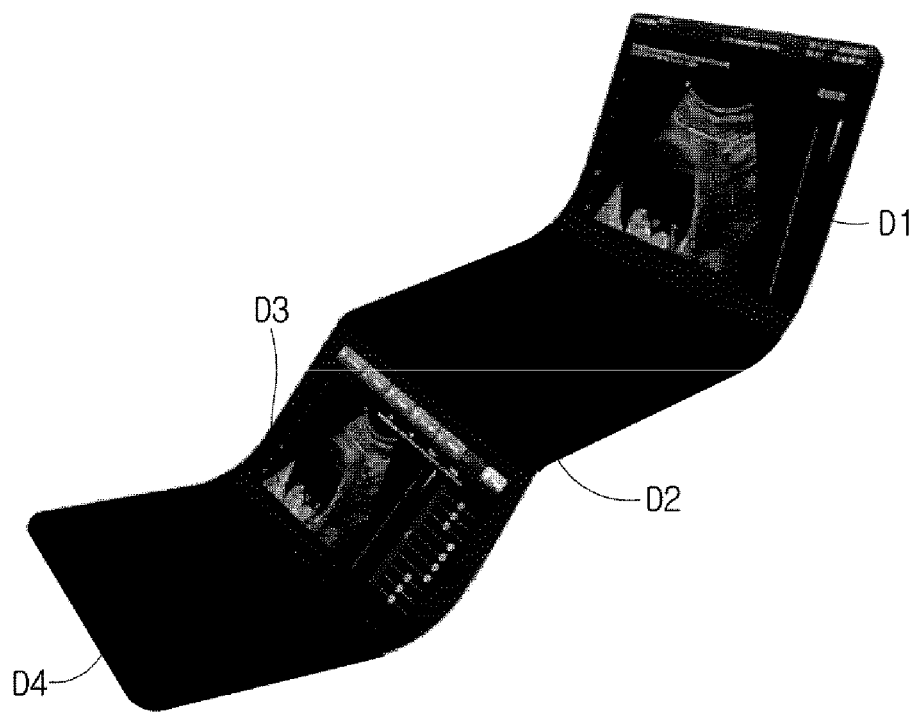
FIG. 24C is a diagram for describing another embodiment of a foldable flexible display.

FIGS. 24A and 24B are diagrams illustrating exteriors of main bodies including flexible displays which are folded twice and three times, respectively. FIG. 24C is a diagram for describing another embodiment of a foldable flexible display.

Referring to FIG. 24A, when the flexible display 250 is folded twice, the flexible display 250 configured of one plane may display an image in three display areas D1, D2, and D3. A layout of the display areas D1, D2, and D3 may be changed according to the control signal of the system controller 240.

Referring to FIG. 24B, when the flexible display 250 is folded three times, the flexible display 250 configured of one plane may display an image in four display areas D1, D2, D3, and D4. A layout of the display areas D1, D2, D3, and D4 may be changed according to the control signal of the system controller 240.

For example, as illustrated in FIG. 24C, the flexible display 250 may power on or off the second area D2 and the fourth display area D4 according to the control signal of the system controller 240. The power on or off of each display area may be controlled according to a user input.

Meanwhile, although it has been described that the flexible display 250 is folded multiple times and the plurality of images are displayed in respective areas in the above-described embodiment, the flexible display 250 may form one or more curved surfaces by performing only bending without folding, the system controller 240 may change the layout according to a bending degree of the flexible display 250, and thus, the physical change of the flexible display 250 is not limited to the above-described example.

In the above-described embodiment, some of the components included in the portable ultrasonic diagnostic apparatus 10 may be implemented using a type of a 'module.' Here, the 'module' refers to software or a hardware component such as a field programmable gate array (FPGA) or an application specific integrated circuit (ASIC) and the module performs any function. However, the module is not limited to the software or the hardware component. The module may be configured to be stored in an addressable storage and to execute one or more processors.

Therefore, as an example, the module includes components such as software components, object-oriented software components, class components, and task components, and processes, functions, attributes, procedures, subroutines, segments of program code, drivers, firmware, microcode, circuits, data, databases, data structures, tables, arrays, and variables. Functions provided in the components and modules may be coupled to a smaller number of components and modules or may be further separated into additional components and modules. In addition, the above-described components and modules may execute one or more CPUs in the device.

Figure 25:
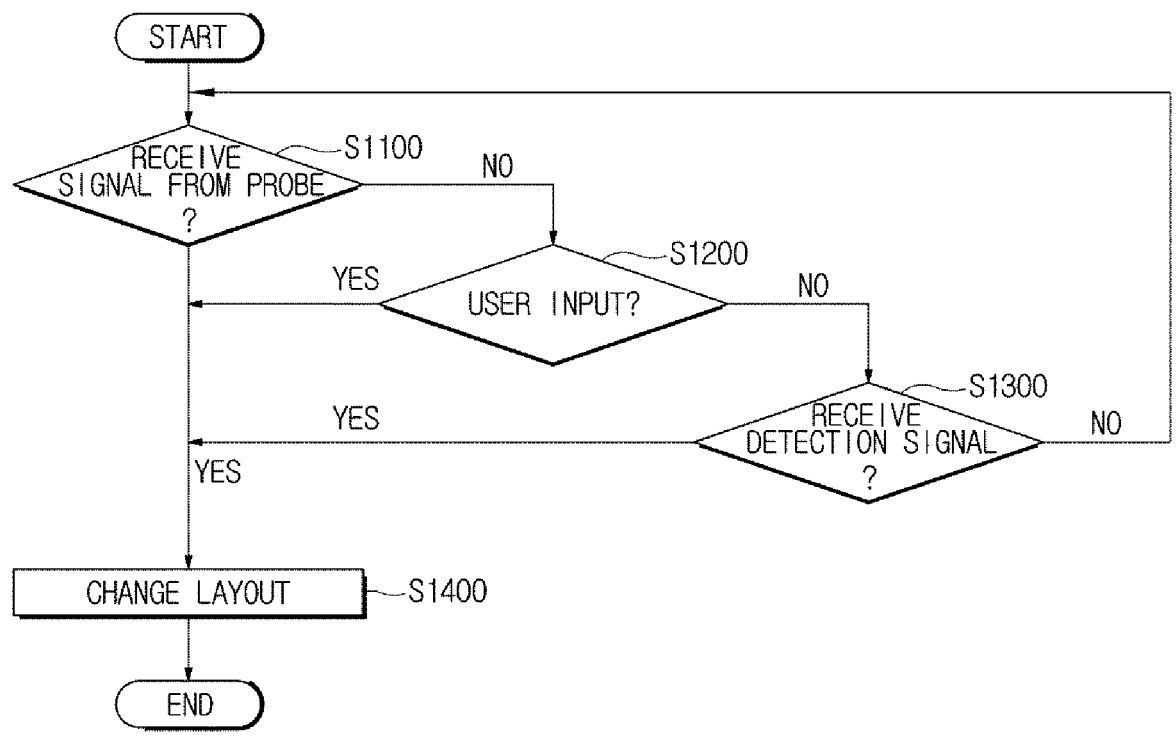
FIG. 25 is a flowchart for describing a method of controlling a portable ultrasonic diagnostic apparatus in accordance with one exemplary embodiment.

Hereinafter, a method of controlling the portable ultrasonic diagnostic apparatus will be described with reference to FIG. 25. FIG. 25 is a flowchart for describing a method of controlling a portable ultrasonic diagnostic apparatus in accordance with one exemplary embodiment.

The portable ultrasonic diagnostic apparatus 10 in accordance with one exemplary embodiment changes a layout of an image displayed in the flexible display 250 according to a situation.

According to one exemplary embodiment, when a main body 200 of the portable ultrasonic diagnostic apparatus 10 receives an electrical signal related to an echo ultrasonic wave from a probe 100 ("yes" in S1100), a flexible display 250 may change a layout of the displayed image (S1400).

Here, the change of the layout may include extension, shrinkage, movement, rotation, or power on/off of at least one display area of the flexible display 250, and enlargement, reduction, or change of the image displayed in the at least one display area.

For example, in the case in which the probe 100 is implemented as a wireless probe and a beamformer 120 and an analog-to-digital converter 125 are included in the probe 100, when the flexible display 250 receives an electrical signal related to an echo ultrasonic wave from the probe 100, the flexible display 250 may change the layout of the image displayed in the flexible display 250.

According to another exemplary embodiment, the user of the portable ultrasonic diagnostic apparatus 10 inputs a control command which changes the layout through the input unit 260 ("yes" in S1200), the flexible display 250 may change the layout of the displayed image (S1400).

For example, when an "emergency mode" hard key is provided in the main body 200 and the user presses the emergency mode hard key, the flexible display 250 may dispose a first area of the flexible display 250 on a front thereof to be suitable for the emergency situation and may display the ultrasonic image in a horizontal direction in the first area.

As another example, when the user inputs a control command for changing the layout through the control panel displayed by the flexible display 250 of the main body 200, the flexible display 250 may change the layout according to the control panel of the user.

According to still another exemplary embodiment, when a sensor is provided in the portable ultrasonic diagnostic apparatus 10 and the sensor generates a detection signal ("yes" in S1300), the flexible display 250 may change the layout of the displayed image corresponding to the detection signal.

For example, when a contact sensor is provided in the main body 200 of the portable ultrasonic diagnostic apparatus 10, the system controller 240 may determine a current state of the flexible display 250 (e.g., contact or non-contact, or folded or not) corresponding to the detection signal of the contact sensor, and may generate a control signal which controls the flexible display 250 according to the determined state of the flexible display 250. The flexible display 250 may change the layout of the displayed image according to the control signal of the system controller 240.

For another example, when an angle sensor is provided in the portable ultrasonic diagnostic apparatus 10, the system controller 240 may determine a current state of the flexible display 250 (e.g., a bending angle of the flexible display 250) corresponding to the detection signal of the angle sensor, and may generate a control signal which controls the flexible display 250 according to the determined state of the flexible display 250. The flexible display 250 may change the layout of the displayed image according to the control signal of the system controller 240.

As described above, although the layout of the flexible display 250 may be changed based on the detection signals of the contact sensor and the angle sensor, the sensor is not limited to the contact sensor and the angle sensor and includes various sensors capable of detecting a physical change of the flexible display 250 such as a gyro sensor, an acceleration sensor, a pressure sensor, a temperature sensor, a deformation sensor, etc.

According to the portable ultrasonic diagnostic apparatuses according to various exemplary embodiments, an image necessary for diagnosing an object is appropriately disposed on a flexible display according to a situation, and thus, the user can intuitively determine an ultrasonic image.

Meanwhile, the above-described method of controlling the portable ultrasonic diagnostic apparatus 10 may be implemented as computer-readable codes in a computer-readable recording medium. The computer-readable recording medium includes all types of recording media in which computer-readable data is stored. Examples of the computer-readable recording medium include a ROM, a RAM, a compact disk ROM (CD-ROM), a magnetic tape, a floppy disk, a flash memory, and an optical data storage. Further, the computer-readable recording medium may be distributed in computer systems connected to a computer communication network, and may be stored and executed as a readable code in a distributed manner.

As is apparent from the above description, the portable ultrasonic diagnostic apparatus in accordance with one exemplary embodiment can appropriately dispose an image necessary for diagnosing an object on a flexible display according to a situation, and thus the user can intuitively determine an ultrasonic image.

The above description of the invention is only exemplary, and it will be understood by those skilled in the art that various modifications can be made without departing from the scope of the present invention and without changing essential features. Therefore, the above-described embodiments should be considered in a descriptive sense only and not for purposes of limitation. For example, each component that is described as a single type may be implemented in a distributed form, and on the other hand, the components that are described as distributed may be implemented in a combined form.

What is claimed is:

1. A portable ultrasonic diagnostic apparatus comprising:
   a probe comprising a beamformer configured to comprise an echo delay unit configured to dynamically set a delay frequency based on a parameter including at least one of a focus point, a steering angle, an aperture size, and a number of activated transducer elements, the probe being configured to transmit an ultrasonic wave towards an object, receive an echo ultrasonic wave reflected by the object, and generate a first digital signal and a second digital signal related to the received echo ultrasonic wave; and
   a main body comprising:
      a flexible display including a first area and a second area divided by a bendable bending position, ad configured to display an ultrasonic image on the first area and a control panel image on the second area,
      an inputter configured to receive a layout change command from a user; and
      a controller configured to change a layout of the first area and the second area,
   wherein,
   the echo delay unit is configured to dynamically set a first delay frequency based on at least one of the focus point, the steering angle, the aperture size, and the number of activated transducer elements to generate the first digital signal,
   the flexible display is configured to display the ultrasonic image of the object on the first area in real time based on the first digital signal,
   when the layout change command from the user for expanding the first area is input to the inputter;

the echo delay unit is configured to dynamically set a second delay frequency based on at least one of the focus point, the steering angle, the aperture size, and the number of activated transducer elements to generate the second digital signal, the controller is configured to expand the first area to the second area and shrink the second area based on the layout change command, and the flexible display is configured to display the ultrasonic image of the object and an extended area including a surrounding area of the object on the first area in real time based on the second digital signal.

2. The apparatus according to claim 1, wherein the controller is configured to move, rotate, power-on, or power-off the first area and the second area of the flexible display.

3. The apparatus according to claim 1, wherein the controller is configured to enlarge, reduce, rotate, or change the ultrasonic image and the control panel image, each displayed on the first area and the second area of the flexible display.

4. The apparatus according to claim 1, wherein the inputter includes an emergency mode button, and the flexible display is configured to display an emergency mode image, configured to provide a predetermined guide to the user on the second area instead of the control panel when the emergency mode button is selected.

5. The apparatus according to claim 4, wherein the emergency mode image includes an image configured to indicate a position of a diagnosis portion of the object.

6. The apparatus according to claim 4, wherein the flexible display is configured to display an image, configured to indicate a position of a diagnosis portion of the object based on at least one of a focused assessment with sonography for trauma (FAST) pericardial, perihepatic, perisplenic, and pelvic (4Ps) reference and a FAST airway, breathing, circulation, and disability (ABCD) reference, on the second area when the emergency mode button is selected.

7. The apparatus according to claim 1, wherein the inputter includes an emergency mode button, and the flexible display is configured to display a text, which provides a predetermined guide to the user, on the second area when the emergency mode button is selected.

8. The apparatus according to claim 1, further comprising a sensor configured to detect a physical change of the flexible display, wherein the controller changes the layout of the first area and the second area according to a detecting signal of the sensor.

9. The apparatus according to claim 8, wherein the sensor includes a contact sensor configured to detect contact of a first end portion of the flexible display which is parallel with the bending position and a second end portion of the flexible display which is parallel with the bending position and an opposite portion of the first end portion.

10. The apparatus according to claim 9, wherein the controller is configured to power off the flexible display when the contact sensor detects the contact of the first portion and the second portion of the flexible display, and display each of the ultrasonic image on the first area and the control panel image on the second area when the contact sensor does not detect the contact of the first portion and the second portion of the flexible display.

11. The apparatus according to claim 8, wherein the sensor includes an angle sensor configured to detect a bending degree of the flexible display.

12. The apparatus according to claim 11, wherein the controller is configured to extend or shrink the first area and the second area based on a detection signal of the angle sensor.

13. The apparatus according to claim 11, wherein the controller is configured to control the flexible display to display a same plane of the object on the first area and the second area of the flexible display when the flexible display is bent a preset angle or more.

14. The apparatus according to claim 11, wherein the controller is configured to control the flexible display to display each of front and rear surfaces or left and right surfaces of a three-dimensional image, or a first ultrasonic image and a second ultrasonic image on the first area and the second area of the flexible display when the flexible display is bent a preset angle or more, wherein the second ultrasonic image is acquired at a time before the first ultrasound image is acquired.

15. The apparatus according to claim 8, wherein the sensor includes at least one of a gyro sensor, an acceleration sensor, a pressure sensor, and a temperature sensor.

16. The apparatus according to claim 1, wherein the flexible display is implemented using a touch screen and displays the control panel image configured to receive a control command from the user through a user interface.

17. The apparatus according to claim 16, wherein the control panel image implements at least one of a keyboard, a mouse, a trackball, a time gain compensation (TGC) control knob, a lateral gain compensation (LGC) control knob, and a paddle.

18. The apparatus according to claim 16, wherein the controller is configured to change a position of the user interface in the control panel image.

19. The apparatus according to claim 1, wherein the probe is a wireless probe.

20. The apparatus according to claim 1, wherein the inputter configured to receive the layout change command simultaneously controls the first area and the second area of the flexible display.

21. The apparatus according to claim 1, wherein the flexible display and the controller are implemented in a portable computer or a portable terminal.

22. The apparatus according to claim 1,
wherein:
the probe further comprises a transducer module, and an analog-to-digital converter, the transducer module is configured to transmit the ultrasonic wave towards the object, and receive the echo ultrasonic wave reflected by the object, and based on the probe being connected to the main body through a cable or through a wireless communication network, the analog-to-digital converter is configured to generate the first digital signal and the second digital signal by converting an analog signal corresponding to the received echo ultrasonic wave.

23. The apparatus according to claim 1, wherein the controller is further configured to rotate the ultrasonic image in the extended first area by a predetermined angle based on the controller receiving the second digital signal related to the echo ultrasonic wave from the probe.

24. A method of controlling a portable ultrasonic diagnostic apparatus, comprising:

transmitting an ultrasonic wave towards an object, receiving an echo ultrasonic wave reflected by the object, and generating a first digital signal and a second digital signal related to the received echo ultrasonic wave;

receiving the first digital signal and the second digital signal related to the echo ultrasonic wave from a probe;

setting by an echo delay unit, at least one of a focus point, a steering angle, an aperture size, and a number of activated transducer elements to generate the first digital signal, and displaying an ultrasonic image of the object on a first area of a flexible display in real time based on the first digital signal;

inputting a user layout change command for expanding the first area into a inputter;

setting, by the echo delay unit, at least one of the focus point, the steering angle, the aperture size, and the number of activated transducer elements to generate the second digital signal;

extending the first area of the flexible display to a second area of the flexible display and shrinking the second area based on receiving the second digital signal from the probe; and displaying, the ultrasonic image of the object and an extended area including a surrounding area of the object on the first area in real time, and a control panel image on the second area of the flexible display according to a changed layout, wherein the portable ultrasonic diagnostic apparatus includes the flexible display including the first area and the second area divided by a bendable bending position.

25. A portable ultrasonic diagnostic apparatus comprising:

a probe configured to: (i) transmit an ultrasonic wave towards an object, (ii) receive an echo ultrasonic wave reflected by the object, and (iii) generate a digital signal related to the received echo ultrasonic wave, a flexible display including a first area and a second area divided by a bendable bedding position, and configured to display an ultrasonic image on the first area and a control panel image on the second area, the control panel image comprising,
  a first virtual icon for receiving a first control command of the portable ultrasonic diagnostic apparatus and
  a second virtual icon for receiving a second control command of the portable ultrasonic diagnostic apparatus;

a controller configured to: (i) change a layout of the first area and the second area, (ii) extend the first area to the second area and shrink the second area based on the controller receiving the digital signal related to the echo ultrasonic wave from the probe, and (iii) remove the second virtual icon from the control panel image and to leave the first virtual icon in the control panel image based on the first area being extended to the second area and the second area being shrunk, wherein:

the first virtual icon corresponds to a trackball, and the second virtual icon corresponds to gain compensation control knobs.

* * * * *

UNITED STATES PATENT AND TRADEMARK OFFICE
CERTIFICATE OF CORRECTION

PATENT NO. : 11,369,347 B2
APPLICATION NO. : 14/854106
DATED : June 28, 2022
INVENTOR(S) : Gil-Ju Jin et al.

It is certified that error appears in the above-identified patent and that said Letters Patent is hereby corrected as shown below:

In the Claims

Column 18, Line 50, Claim 1:
"area divided by a bendable bending position, ad"
Should read:
-- area divided by a bendable bending position, and --

Signed and Sealed this
Fourth Day of April, 2023

Katherine Kelly Vidal
*Director of the United States Patent and Trademark Office*